(12) United States Patent
Kawaoka et al.

(10) Patent No.: US 8,877,209 B2
(45) Date of Patent: *Nov. 4, 2014

(54) RECOMBINANT INFLUENZA VECTORS WITH TANDEM TRANSCRIPTION UNITS

(75) Inventors: Yoshihiro Kawaoka, Middleton, WI (US); Gabriele Neumann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 214 days.

This patent is subject to a terminal disclaimer.

(21) Appl. No.: 13/113,244

(22) Filed: May 23, 2011

(65) Prior Publication Data

US 2011/0300604 A1 Dec. 8, 2011

Related U.S. Application Data

(63) Continuation of application No. 11/283,498, filed on Nov. 18, 2005, now Pat. No. 7,968,101.

(60) Provisional application No. 60/629,665, filed on Nov. 19, 2004.

(51) Int. Cl.
| | |
|---|---|
| *A01N 63/00* | (2006.01) |
| *A61K 39/00* | (2006.01) |
| *A61K 39/12* | (2006.01) |
| *A61K 39/145* | (2006.01) |
| *A61K 45/00* | (2006.01) |
| *C12Q 1/70* | (2006.01) |
| *C12P 1/00* | (2006.01) |
| *C12P 19/34* | (2006.01) |
| *C12N 7/02* | (2006.01) |
| *C12N 15/00* | (2006.01) |
| *C12N 15/74* | (2006.01) |
| *A61K 48/00* | (2006.01) |
| *C12N 15/86* | (2006.01) |
| *C12N 7/00* | (2006.01) |
| *A61K 39/285* | (2006.01) |

(52) U.S. Cl.
CPC ......... *C12N 15/86* (2013.01); *A61K 2039/5254* (2013.01); *A61K 48/0091* (2013.01); *A61K 2039/525* (2013.01); *A61K 39/145* (2013.01); *C12N 2760/16234* (2013.01); *C12N 2760/16161* (2013.01); *C12N 2760/16151* (2013.01); *C12N 2760/16251* (2013.01); *A61K 2039/5256* (2013.01); *C12N 2760/16134* (2013.01); *C12N 2760/16143* (2013.01); *A61K 2039/5252* (2013.01); *C12N 2760/16051* (2013.01); *C12N 7/00* (2013.01); *C12N 2760/16243* (2013.01); *C12N 2760/16043* (2013.01); *C12N 2760/16261* (2013.01)
USPC ............... 424/206.1; 424/184.1; 424/204.1; 424/205.1; 424/209.1; 424/93.6; 424/93.2; 424/281.1; 435/5; 435/41; 435/91.33; 435/239; 435/320.1; 435/476; 435/489

(58) Field of Classification Search
CPC ................ C07K 16/1018; C12N 7/00; C12N 2760/16134; C12N 15/86; C12N 15/85; C12N 2760/16143; C12N 2760/16151; C12N 2760/16123; C12N 2760/16162; C12N 2710/10343; C12N 2760/16222; C12N 2760/16243; C12N 2760/16152; C12N 2760/16043; C12N 2760/16252; C12N 2760/16022; C12N 2760/16121; C12N 2760/16132; C12N 2760/16211; C12N 2760/16223; A61K 39/145; G01N 33/56983; G01N 2333/11
See application file for complete search history.

(56) References Cited

U.S. PATENT DOCUMENTS

| | | | |
|---|---|---|---|
| 4,071,618 A | 1/1978 | Konobe et al. | |
| 4,659,569 A | 4/1987 | Mitsuhashi et al. | |
| 5,166,057 A | 11/1992 | Palese et al. | |
| 5,578,473 A | 11/1996 | Palese et al. | |
| 5,716,821 A | 2/1998 | Wertz et al. | |
| 5,786,199 A | 7/1998 | Palese | |
| 5,789,229 A | 8/1998 | Wertz et al. | |
| 5,820,871 A | 10/1998 | Palese et al. | |
| 5,840,520 A | 11/1998 | Clarke et al. | |
| 5,854,037 A | 12/1998 | Palese et al. | |
| 6,001,634 A | 12/1999 | Palese et al. | |
| 6,033,886 A | 3/2000 | Conzelmann | |
| 6,146,642 A | 11/2000 | Garcia-Sastre et al. | |
| 6,271,011 B1 | 8/2001 | Lee et al. | |
| 6,358,733 B1 | 3/2002 | Motwani et al. | |
| 6,872,395 B2 | 3/2005 | Kawaoka | |
| 7,226,774 B2 | 6/2007 | Kawaoka | |
| 7,968,101 B2 | 6/2011 | Kawaoka et al. | |
| 2002/0164770 A1 | 11/2002 | Hoffmann | |
| 2003/0035814 A1 | 2/2003 | Kawaoka et al. | |
| 2004/0002061 A1 | 1/2004 | Kawaoka | |
| 2004/0029251 A1 | 2/2004 | Hoffman et al. | |
| 2004/0219170 A1 | 11/2004 | Kawaoka | |
| 2004/0241139 A1 | 12/2004 | Hobom et al. | |

(Continued)

FOREIGN PATENT DOCUMENTS

| | | |
|---|---|---|
| EP | 0702085 A1 | 3/1996 |
| EP | 0704533 A1 | 4/1996 |

(Continued)

OTHER PUBLICATIONS

Result 17, NCBI Blast nucleotide search of SEQ ID No. 2, database "nr", 2006.

(Continued)

*Primary Examiner* — Benjamin P Blumel

(74) *Attorney, Agent, or Firm* — Schwegman Lundberg & Woessner, P.A.

(57) ABSTRACT

The invention provides a composition useful to prepare influenza viruses, e.g., in the absence of helper virus, using vectors which include tandem transcription cassettes containing PolI and/or PolII promoters.

10 Claims, 6 Drawing Sheets

(56) References Cited

U.S. PATENT DOCUMENTS

| | | |
|---|---|---|
| 2005/0037487 A1 | 2/2005 | Kawaoka et al. |
| 2006/0057116 A1 | 3/2006 | Kawaoka et al. |
| 2006/0134138 A1 | 6/2006 | Kawaoka et al. |
| 2006/0166321 A1 | 7/2006 | Kawaoka et al. |
| 2007/0141699 A1 | 6/2007 | Kawaoka |

FOREIGN PATENT DOCUMENTS

| | | |
|---|---|---|
| EP | 1201760 A1 | 5/2002 |
| WO | WO-9802530 A1 | 1/1998 |
| WO | WO-9848834 A1 | 11/1998 |
| WO | WO-9853078 A1 | 11/1998 |
| WO | WO-0060050 A2 | 10/2000 |
| WO | WO-0179273 A2 | 10/2001 |
| WO | WO-03068923 A2 | 8/2003 |
| WO | WO-2004112831 A2 | 12/2004 |
| WO | WO-2005028658 A2 | 3/2005 |
| WO | WO-2007044024 A2 | 4/2007 |

OTHER PUBLICATIONS

Result 7, NCBI Blast nucleotide search of SEQ ID: 1, database "nr", 2006.
Result 1, NCBI Blast nucleotide search of SEQ ID No. 3, database "nr"; Result 4, NCBI Blast nucleotide search of SEQ ID No. 4, database "nr", 2006.
Result 2, NCBI Blast nucleotide search of SEQ ID No. 5, database "nr"; Result 4, NCBI Blast nucleotide search of SEQ ID No. 6, database "nr", 2006.
Results 1, NCBI Blast nucleotide search of SEQ ID No. 7, database "nr"; Result 1, NCBI Blast nucleotide search of SEQ ID No. 8, database "nr", 2006.
"U.S. Appl. No. 11/283,498, Non Final Office Action mailed Sep. 3, 2009", 5 pgs.
"U.S. Appl. No. 11/283,498, Non Final Office Action mailed Jul. 9, 2007", 7 pgs.
"U.S. Appl. No. 11/283,498, Non-Final Office Action mailed Jan. 23, 2008", 20 pgs.
"U.S. Appl. No. 11/283,498, Non-Final Office Action mailed Apr. 29, 2010", 10 pgs.
"U.S. Appl. No. 11/283,498, Notice of Allowance mailed Feb. 23, 2011", 9 pgs.
"U.S. Appl. No. 11/283,498, Response filed Jan. 4, 2010 to Non Final Office Action mailed Sep. 3, 2009", 12 pgs.
"U.S. Appl. No. 11/283,498, Response filed Oct. 28, 2010 to Non Final Office Action mailed Apr. 29, 2010", 13 pgs.
"U.S. Appl. No. 11/283,498, Response filed Nov. 7, 2007 to Office Action mailed Jul. 9, 2007", 17 pgs.
"U.S. Appl. No. 11/283,498, Response filed Apr. 16, 2007 to Restriction Requirement mailed Oct. 16, 2006", 17 pgs.
"U.S. Appl. No. 11/283,498, Response filed Jul. 22, 2008 to Non Final Office Action mailed Jan. 23, 2008", 12 pgs.
"U.S. Appl. No. 11/283,498, Restriction Requirement mailed Oct. 16, 2006", 6 pgs.
"U.S. Appl. No. 11/283,498, Supplemental Amendment Response to Non Final Office Action mailed Oct. 28, 2010", 11 pgs.
"Application Serial No. 200580046922.5, Office Action mailed Jul. 24, 2009", 12 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf.html, (Observed Feb. 22, 2003), 2 pgs.
"Confirmed Cases of Avian Influenza A(H5N1)", World Health Organization, (Jan. 28, 2004), 1 pg.
"Eurasian Application Serial No. 200701097,Office Action mailed Sep. 4, 2008", OAR-MISC, 2.
"Eurasion Application Serial No. 200701097, Office Action mailed Jun. 16, 2009", 3 pgs.
"International Application Serial No. PCT/US2005/041991, International Search Report mailed Jun. 4, 2007", 5 pgs.

"Israel Application Serial No. 183026, Office Action Mailed on Feb. 9, 2009", 2 pgs.
"New Zealand Application Serial No. 555245, First Examination Report Mailed on Aug. 26, 2008", 2 pgs.
"PCT Application Serial No. PCT/US2005/041991, International Preliminary Report on Patentability / Written Opinion mailed Jul. 19, 2007", 8 pgs.
"RNA World", http://faculty.uca.edu/~benw/biol4415/lecture10a/tsId003.htm, (Observed Feb. 25, 2003), 1 pg.
"Written Opinion for corresponding PCT Application No. PCT/US2005/041991", (Jun. 4, 2007), 6 pgs.
555245, "New Zealand application No. 555245 subsiquent examiner report mailed on Jul. 3, 2009", 1.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Beare, A. S., "Trials in Man With Live Recombinants Made From A/PR/8/34 (H0 N1) and Wild H3 N2 Influenza Viruses", The Lancet, 2(7938), (1975), 729-732.
Bilsel, P., et al., "Mutations in the Cytoplasmic Tail of Influenza A Virus Neuraminidase Affect Incorporation into Virions", Journal of Virology, 67(11), (Nov. 1993), 6762-6767.
Blount, K. F., et al., "The Hammerhead Ribozyme", Biochemical Society Transactions, 30(6), (2002), 1119-1122.
Boyer, J. C., et al., "Infectious transcripts and cDNA clones of RNA viruses", Virology, 198(2), (Feb. 1994), 415-426.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brands, R., et al., "Influvac: A Safe Madin Darby Canine Kidney (MDCK) Cell Culture-Based Influenza Vaccine", Dev. Biol. Stand., 98, (1999), 93-100.
Bridgen, A., "Rescue of a Segmented Negative-Strand RNA Virus Entirely From Cloned Complementary DNAs", Proc. Natl. Acad. Sci. USA, 93, (1996), 15400-15404.
Bruhl, P., et al., "Humoral and Cell-Mediated Immunity to Vero Cell-Derived Influenza Vaccine", Vaccine, 19, (2001), 1149-1158.
Buchholz, U. J., et al., "Generation of Bovine Respiratory Syncytial Virus (BRSV) From cDNA: BRSV NS2 is Not Essentiial for Virus Replication in Tissue Culture, and the Human RSV Leader Region Acts as a Functional BRSV Genome Promoter", Journal of Virology, 73(1), (1999), 251-259.
Bukreyev, A., et al., "Recovery of infectious respiratory syncytial virus expressing an additional, foreign gene", Journal of Virology, 70(10), (Oct. 1996), 6634-6641.
Cardona, C. J., "Avian Influenza", http://www.vetmed.ucdavis.edu/vetex/INF-PO__AvianInfluenzaFS.html, ((Observed Feb. 22, 2003), 3 pgs.
Castrucci, M. R, et al., "Attenuation of Influenza a Virus by Insertion of a Foreign Epitope into the Neuraminidase", Journal of Virology, 66(8), (1992), 4647-4653.
Castrucci, M. R., et al., "Biologic Importance of Neuraminidase Stalk Length in Influenza A Virus", Journal of Virology, vol. 67, No. 2, (1993), 759-764.
Castrucci, M. R., et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, vol. 68(6), (Jun. 1994), 3486-3490.
Castrucci, M. R, et al., "Reverse genetics system for generation of an influenza A virus mutant containing a deletion of the carboxyl-terminal residue of M2 protein.", J Virol., 69(5), (May 1995), 2725-8.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.

(56) References Cited

OTHER PUBLICATIONS

Claas, E C. J., et al., "Human Influenza A H5N1 Virus Related to a Highly Pathogenic Avian Influenza Virus", The Lancet, 351, (1998), 472-477.
Clarke, D. K., et al., "Rescue of Mumps Virus From cDNA", Journal of Virology, 74(10), (2000), 4831-4838.
Collins, P. L., et al., "Chapter 41—Parainfluenza Viruses", In: Fields Virology, edited by Fields, B. N., et al. (3rd Edition, 1996, Lippincott-Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
Crescenzo-Chaigne, Bernadette, et al., "Comparative analysis of the ability of the polymerase complexes of influenza viruses type A, B and C to assemble into functional RNPs that allow expression and replication of heterotypic model RNA templates in vivo", Virology, 265(2), (Dec. 1999), 342-353.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Desselberger, Ulrich, et al., "The 3' and 5'-terminal sequences of influenza A, B and C virus RNA segments are highly conserved and show partial inverted complementarity", Gene, 8 (3), (Feb. 1980), 315-328.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dollenmaier, G., et al., "Membrane-Associated Respiratory Syncytial Virus F Protein Expressed From A Human Rhinovirus Type 14 Vector Is Immunogenic", Virology, 281(2), (Mar. 15, 2001), 216-230.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Du, Q., "Ribozyme Enzymology", http://academic.brooklyn.cuny.edu/chem/zhuang/QD/toppage1.htm, (Observed Feb. 25, 2003), 8 pgs.

Dunn, E. F., et al., "Transcription of a recombinant bunyavirus RNA template by transiently expressed bunyavirus proteins", Virology, 211(1), (1995), 133-143.
Durbin, A. P, et al., "Human Parainfluenza Virus Type 3 (PIV3) Expressing The Hemagglutinin Protein Of Measles Virus Provides A Potential Method For Immunization Against Measles Virus and PIV3 In Early Infancy", Journal of Virology, 74(15), (Aug. 2000), 6821-6831.
Durbin, A. P., et al., "Recovery of infectious human parainfluenza virus type 3 from cDNA", Virology, 235(2), (Sep. 1, 1997), 323-332.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Fahey, J. L., "Status of Immune-Based Therapies in HIV Infection and Aids", Clinincal and Experimental Immunology, 88(1), (1992), 1-5.
Flandorfer, A., et al., "Chimeric Influenza A Viruses with a Functional Influenza B Virus Neuraminidase or Hemagglutinin", Journal of Virology, 77(17), (Sep. 2003), 9116-9123.
Fodor, E., et al., "Rescue of Influenza A Virus from Recombinant DNA", Journal of Virology, 73(11), XP002151487; ISSN:0022-538X, (Nov. 1999), 9679-9682.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5), (2004), 1356-1361.
Fujii, Y, et al., "The packaging of influenza viral genome", Virus, 52 (1), Uirusu (Japanese Journal Name), (Jun. 2002), 203-206.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of Influenza A Virus", Dev. Biol. Stand. vol. 82, (1994), 237-246.
Garcia-Sastre, Adolfo, et al., "Use of a Mammalian Internal Ribosomal Entry Site Element for Expression of a Foreign Protein by a Transfectant Influenza Virus", Journal of Virology, 68(10), (Jun. 30, 1994), 6254-6261.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", Newsday.com, (Feb. 20, 2003), 3 pgs.
Gerdil, C., "The Annual Production Cycle for Influenza Vaccine", Vaccine, 21, (2003), 1776-1779.
Ghate, Anita A, et al., "Influenza Type B Neuraminidase Can Replace the Function of Type A Neuraminidase", Virology, 264 (2), (Nov. 1999), 265-277.
Gilleland, H. E, et al., "Chimeric Influenza Virus Incorporating Epitopes of Outer Membrane Protein F as a Vaccine Against Pulmonary Infection with *Pseudomonas aeruginosa*", Behring Inst. Mitt. 98, (Feb. 1997), 291-301.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Grosfeld, H., et al., "RNA Replication by Respiratory Syncytial Virus (RSV) Is Directed by the N, P, and L Proteins; Transcription Also

(56) References Cited

OTHER PUBLICATIONS

Occurs Under These Conditions but Requires RSV Superinfection for Efficient Synthesis of Full-Length mRNA", Journal of Virology, 69(9), (1995), 5677-5686.

Halperin, S. A., et al., "Safety and Immunogenicity of a Trivalent, Inactivated, Mammalian Cell Culture-Derived Influenza Vaccine in Healthy Adults, Seniors, and Children", Vaccine, 20, (2002), 1240-1247.

Hatada, E., et al., "Binding of Influenza A Virus NS1 Protein to dsRNA in vitro", Journal of General Virology, 73, (1992), 3325-3329.

He, B., et al., "Recovery of infectious SV5 from cloned DNA and expression of a foreign gene", Virology, 237(2), (1997), 249-260.

Hiti, A. L., et al., "P03470—Neuraminidase", Entrez Protein Database, http://www.ncbi.nlm.nih.gov/entrez/viewer.fcgi?db=protein&val=84028231, (1982), 730-734.

Hoffman, E., et al., "Ã????AmbisenseÃ???? Approach for the Generation of Influenza A Virus: vRNA and mRNA Synthesis from One Template", Virology 267(2), (Feb. 15, 2006), 310-317.

Hoffman, M. A., et al., "An Infectious Clone of Human Parainfluenza Virus Type 3", Journal of Virology, 71(6), (1997), 4272-4277.

Hoffmann, E., et al., "Ambisense Approach for the Generation of Influenza A Virus: vRNA and mRNA Synthesis from One Template", Virology, 267, (2000), 310-317.

Hoffmann, E., et al., ""Ambisense" approach for the generation of influenza A virus: vRNA and mRNA synthesis from one template.", Virology, 267(2), (Feb. 15, 2000), 310-7.

Hoffmann, E., et al., "A DNA Transfection System for Generation of Influenza A Virus Eight Plasmids", Proceedings of National Academy of Science of USA; 97(11), (Apr. 23, 2000), 6108-6113.

Hoffmann, E., et al., "Eight-Plasmid System for rapid Generation of influenza Virus Vaccines", Vaccine 20—(25-26), (Aug. 19, 2002), 3165-3170.

Hoffmann, E., et al., "Rescue of Influenza B Virus from Eight Plasmids", Proceedings of the National Academy of Sciences of USA, National Academy of Science, 99(17), (Aug. 20, 2002), 11411-11416.

Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.

Huang, T.-S., et al., "Determination of Influenza Virus Proteins Required for Genome Replication", Journal of Virology, 64(11), (1990), 5669-5673.

Hughes, Mark T, "Adaptation of Influenza A Viruses to Cells Expressing Low Levels of Sialic Acid Leads to Loss of Neuraminidase Activity", Journal of Virology, 75 (8), (Apr. 2001), 3766-3770.

Hughes, Mark T, "Influenza A Viruses Lacking Sialidase Activity Can Undergo Multiple Cycles of Replication in Cell Culture, Eggs, or Mice", Journal of Virology, 74 (11), (Jun. 2000), 5206-5212.

Kaplan, G., et al., "In vitro Synthesis of Infectious Poliovirus RNA", Proc. Natl. Acad. Sci. USA, 82, (1985), 8824-8428.

Katinger, D., et al., "Attenuated Influenza Viruses as a Vector for Mucosal Immunization Against HIV-1", Vaccines, 97, Cold Spring Harbor, (1997), 315-319.

Kato, A., et al., "Initiation of Sendai Virus Multiplication From Transfected cDNA or RNA With Negative or Positive Sense", Genes to Cells, 1, (1996), 569-579.

Kawaoka, Y., "Mutant Cells With Altered Sialic Acid", U.S. Appl. No. 11/644,179, filed Dec. 22, 2006, 51 pgs.

Kijima, H., et al., "Therapeutic Application of Ribozymes", Pharmac. Ther., 68(2), (1995), 247-267.

Kimura, N., et al., "An In Vivo Study of the Replication Origin in the Influenza Virus Complementary RNA", The Journal of Biochemistry, 113(1), (1993), 88-92.

Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.

Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.

Kistner, O., et al., "Development of a Mammalian Cell (Vero) Derived Candidate Influenza Virus Vaccine", Vaccine, 16, (1998), 960-968.

Kistner, O., et al., "Development of a Vero Cell-Derived Influenza Whole Virus Vaccine", Dev. Biol. Stand., 98, (1999), 101-110.

Kobayashi, M., et al., "Reconstitution of Influenza Virus RNA Polymerase From Three Subunits Expressed Using Recombinant Baculovirus System", Virus Research, 22, (1992), 235-245.

Konarska, M. M., et al., "Structure of RNAs Replicated by the DNA-Dependent T7 RNA Polymerase", Cell, 63(2), (1990), 609-618.

Koopmans, M., et al., "Transmission of H7N7 Avian Influenza Virus to Human Beings During a Large Outbreak in Commercial Poultry Farms in the Netherlands", The Lancet, 363, (2004), 587-593.

Krystal, M., et al., "Influenza B/Lee/40, hemagglutinin (seg 4), complete segment.", Database Accession No. K00423, Entrez Nucleotide Database, http://www.ncbi.nlm.nih.gov/entrez/viewer.fcgi?db=nucleotide&val=325175, (Apr. 25, 1990).

Kumar, P. K. R., et al., "Artificial Evolution and Natural Ribozymes", The FASEB Journal, 9, (1995), 1183-1195.

Kunkel, T. A., "Rapid and Efficient Site-Specific Mutagenesis Without Phenotypic Selection", Proc. Natl. Acad. Sci. USA, 82, (1985), 488-492.

Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.

Lawson, N. D., "Recombinant Vesicular Stomatitis Viruses From DNA", Proc. Natl. Acad. Sci. USA, 92(10), (1995), 4477-4481.

Laxman, B., "Noninvasive Real-Time Imaging of Apoptosis", PNAS, 99(26), (2002), 16551-16555.

Levis, R., et al., "Deletion Mapping of Sindbis Virus DI RNAs Derived From cDNAs Defines the Sequences Essential for Replication and Packaging", Cell, 44, (1986), 137-145.

Li, S., et al., "Influenza A Virus Transfectants with Chimeric Hemagglutinins containing Epitopes from different subtypes", Journal of Virology, (1992), 399-404.

Liu, Chongguang, "Influenza type A virus neuraminidase does not play a role in viral entry, replication, assembly, or budding.", Journal of Virology, 69(2), (Feb. 1995), 1099-106.

Liu, Chongguang, "Selection and characterization of a neuraminidase-minus mutant of influenza virus and its rescue by cloned neuraminidase genes.", Virology, 194(1), (1993), 403-407.

Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.

Luytjes, W., "Amplification, Expression, and Packaging of a Foreign Gene by Influenza Virus", Cell, 59(6), (1989), 1107-1113.

Mena, I., "Rescue of a Synthetic Choramphenicol Acetyltransferase RNA into influenza Virus-Like Particles obtained from recombinant plasmids", Journal of Virology, 70(8), (1996), 5016-5024.

Mena, I., et al., "Synthesis of Biologically Active Influenza Virus Core Proteins Using a Vaccinia Virus-T7 RNA Polymerase Expression System", Journal of General Virology, 75, (1994), 2109-2114.

Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.

Mitnaul, Lyndon J, et al., "Balanced Hemagglutinin and Neuraminidase Activities are Critical for Efficient Replication of Influenza A Virus", Journal of Virology, 74 (13), (Jul. 2000), 6015-6020.

Moss, B., et al., "New Mammalian Expression Vectors", Nature, 348, (1990), 91-92.

Moyer, S. A., et al., "Assembly and Transcription of Synthetic Vesicular Stomatitis Virus Nucleocapsids", Journal of Virology, 65(5), (1991), 2170-2178.

Muster, T., "An Influenza A Virus Containing Influenza B Virus 5' and 3' Noncoding Regions on the Neuraminidase Gene is Attenuated in Mice", Proceeding of the National Academy of Sciences USA, 88, (Jun. 1991), 5177-5181.

(56) References Cited

OTHER PUBLICATIONS

Naito, S., et al., "Function and Structure of RNA Polymerase From Vesicular Stomatitis Virus", The Journal of Biological Chemistry, 251(14), (1976), 4307-4314.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "A decade after the generation of a negative-sense RNA virus from cloned cDNA Ã?? what have we learned", Journal of General Virology; 83, (2002), 2635-2662.
Neumann, G., et al., "An Improved Reverse Genetics System for Influenza A Virus Generation and Its Implications for Vaccine Production", Proc. Natl. Acad. Sci. USA, 102(46), (2005), 16825-16829.
Neumann, G., et al., "Generation of Influenza A Virus from Cloned cDNA-historical perspective and outlook for the new millennium", Reviews in Medical Virology; 12(1), (Jan. 2, 2002), 13-30.
Neumann, G., et al., "Generation of Influenza A Viruses Entirely from Cloned cDNAs", Proc. Natl. Acad. Sci. USA, 96(16), (Aug. 1999), 9345-9350.
Neumann, G., et al., "Genetic Engineering of Influenza and Other Negative-Strand RNA Viruses Containing Segmented Genomes", Advances in Virus Research, 53, (1999), 265-300.
Neumann, G., et al., "Plasmid-driven formation of Influenza Virus-like Particles", Journal of Virology; 74(1), (2000), 547-551.
Neumann, G., et al., "Reverse genetics of influenza virus.", Virology, 287(2), (Sep. 1, 2001), 243-50.
Neumann, G., et al., "RNA Polymerase I-Mediated Expression of Influenza Viral RNA Molecules", Virology, 202(1), (1994), 477-479.
Neumann, Gabriele, et al., "Influenza A virus NS2 protein mediates vRNP nuclear export through NES-independent interaction with hCRM1", The EMBO Journal, 19 (24), (2000), 6751-6758.
Neumann, Gabriele, et al., "Mutational Analysis of Influenza Virus Promoter Elements In Vivo", Journal of General Virology (1995), 76, (Feb. 24, 1995), 1709-1717.
Nicolson, C., et al., "Generation of Influenza Vaccine Viruses on Vero Cells by Reverse Genetics: an H5N1 Candidate Vaccine Strain Produced Under a Quality System", Vaccine, 23, (2005), 2943-2952.
Odagiri, T., et al., "Nucleotide Sequence of the PA Gene of Influenza A/WSN/33 (H1N1)", Nucleic Acids Research, 18 (3), Department of Virology, (Jan. 9, 1990).
Ozaki, H., et al., "Generation of High-Yielding Influenza A Viruses in African Green Money Kidney (Vero) Cells by Reverse Genetiics", Journal of Virology, 78(4), (2004), 1851-1857.
Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98, (1999), 133-134.
Palese, P., "Negative-Strand RNA Viruses: Genetic Engineering and Applications", Proc. Natl. Acad. Sci. USA, 93(21), (1996), 11354-11358.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Peiris, J. S. M., et al., "Re-Emergence of Fatal Human Influenza A Subtype H5N1 Disease", The Lancet, 363, (2004), 617-619.
Pekosz, A., "Commentary—Reverse Genetics of Negative-Strand RNA Viruses: Closing the Circle", Proc. Natl. Acad. Sci. USA, 96, (1999), 8804-8806.
Percy, N., et al., "Expression of a Foreign Protein by Influenza A Virus", Journal of Virology, 68(7), (1994), 4486-4492.
Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.
Piatti, G., "Identification Of Immunodominant Epitopes In The Filamentous Hemagglutinin Of *Bordetella pertusis*", FEMS Immunology and Medical Microbiology, 23(3), (Mar. 1999), 235-241.
Pleschka, S., et al., "A Plasmid-Based Reverse Genetics System for Influenza A Virus", Journal of Virology, 70(6), (1996), 4188-4192.
Pley, H. W., et al., "Three-Dimensional Structure of a Hammerhead Ribozyme", Nature, 372, (1994), 68-74.
Portela, Agustin, et al., "Replication of orthomyxoviruses", Advances in Virus Research, 54, (1999), 319-348.
Potter, C. W., "Chapter 1—Chronicle of Influenza Pandemics", In: Textbook of Influenza, Nicoholson, K. G., et al., Editors, (Blackwell Scientific Publication), (1998), 3-18.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981).
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Roberts, A., et al., "Minireview—Recovery of Negative-Strand RNA Viruses From Plasmid DNAs: A Positive Approach Revitalizes a Negative Field", Virology, 247(1), (1998), 1-6.
Rodrigues, M., et al., "Influenza and vaccinia viruses expressing malaria CD8+ T and B cell epitopes. Comparison of their immunogenicity and capacity to induce protective immunity", J Immunol., 153(10), (Nov. 15, 1994), 4636-48.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Satterlee, B., "Production of H5N1 avian influenza virus vaccine by plasmid-based reverse genetics technology", Basic Biotechnology eJournal, vol. 4, pp. 93-98, (2008), 93-98 Pgs.
Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17 (5), (1998), 1289-1296.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.
Shortridge, K. F., et al., "Characterization of Avian H5N1 Influenza Viruses From Poultry in Hong Kong", Virology, 252, (1998), 331-342.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.

(56) References Cited

OTHER PUBLICATIONS

Strobel, I., et al., "Efficient Expression Of The Tumor-Associated Antigen MAGE-3 In Human Dendritic Cells, Using An Avian Influenza Virus Vector", Human Gene Therapy, 11(16), (Nov. 1, 2000), 2207-2218.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Characterization of an Avian Influenza A (H5N1) Virus Isolated From a Child With a Fatal Respiratory Illness", Science, 279, (1998), 393-396.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugawara, K., et al., "Development of Vero Cell-Derived Inactivated Japanese Encephalities Vaccine", Biologicals, 30, (2002), 303-314.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.
Taylor, J., et al., "Newcastle Disease Virus Fusion Protein Expressed in a Fowlpox Virus Recombinant Confers Protection in Chickens", Journal of Virology, 64(4), (1990), 1441-1450.
Thompson, W. W., et al., "Mortality Associated With Influenza and Respiratory Syncytial Virus in the United States", JAMA, 289(2), (2003), 179-186.
Ward, C. D., et al., "Direct Measurement of the Poliovirus RNA Polymerase Error Frequency In Vitro", Journal of Virology, 62(2), (1988), 558-562.
Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Wood, J. M., et al., "From Lethal Virus to Life-Saving Vaccine: Developing Inactivated Vaccines for Pandemic Influenza", Nature Reviews Microbiology, 2(10), (2004), 842-847.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yang, Ping, "Hemagglutinin specificity and neuraminidase coding capacity of neuraminidase-deficient influenza viruses.", Virology, 229(1), (1997), 155-165.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.
Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zobel, A., et al., "RNA Polymerase I Catalysed Transcription of Insert Viral cDNA", Nucleic Acids Research, 21(16), (1993), 3607-3614.

RECOMBINANT INFLUENZA VECTORS WITH TANDEM TRANSCRIPTION UNITS

CROSS-REFERENCE TO RELATED APPLICATIONS

This application is a continuation of U.S. patent application Ser. No. 11/283,498, filed Nov. 18, 2005, now U.S. Pat. No. 7,968,101, which claims the benefit of the filing date of U.S. application Ser. No. 60/629,665, filed Nov. 19, 2004, the disclosures of which are incorporated by reference herein.

STATEMENT OF GOVERNMENT RIGHTS

This invention was made with a grant from the Government of the United States of America (grant AI047446 from the National Institute of Allergy and Infectious Diseases Public Health Service). The Government may have certain rights in the invention.

BACKGROUND

Influenza epidemics and pandemics continue to claim human lives and impact the global economy. In the United States alone, influenza causes an estimated 50,000 deaths annually (Thompson et al., 2003), while global pandemics can result in millions of influenza-related deaths. A classic example is the so-called 'Spanish influenza', which killed an estimated 40-50 million people worldwide in 1918-1919 (Potter, 1998). The threat imposed by influenza virus has been further elevated with the recent introductions of avian influenza viruses into the human population. Avian influenza viruses were long thought not to be directly transmissible to humans and cause lethal outcomes. However, this perception changed in 1997, when 18 Hong Kong residents were infected by a wholly avian influenza virus of the H5N1 subtype, that resulted in 6 deaths (Subbarao et al., 1998; Claas et al., 1998). Over the next few years, several other cases of direct avian-to-human transmission were reported (Peiris et al., 2004; Fouchier et al., 2004; Koopsman et al., 2004), including the ongoing outbreak of highly pathogenic H5N1 influenza viruses in several Asian countries that has claimed 41 lives of 54 infected individuals as of Jan. 26, 2005 (WHO, 2004). The increasing numbers of human H5N1 virus infections, together with a high mortality rate and possible human-to-human transmission, make the development of vaccines to these viruses essential.

In the United States, two influenza vaccines are licensed for human use: an inactivated vaccine and a live attenuated vaccine virus. The production of influenza virus vaccines relies on reassortment (Gerdil, 2003), which requires coinfection of cells with a circulating wild-type strain that provides the hemagglutinin (HA) and neuraminidase (NA) segments and either A/PR/8/34 (PR8) virus (an attenuated human virus that provides high-growth properties in eggs) or a live attenuated virus that provides the attenuated phenotype. The selection of the desired "6+2" reassortants (i.e., those containing the HA and NA gene segments of the circulating wild-type strain in the genetic background of PR8 or live attenuated virus) is time-consuming and cumbersome. Moreover, the need for reassortment and selection, as well as the inability of some reassortant viruses to grow to high titers, have resulted in delays in vaccine production.

For influenza A and B viruses, highly efficient reverse genetics systems are now in place that allow the generation of these viruses from cloned cDNA (Neumann et al., 1999; Hoffmann et al., 2002; Fodor et al., 1999; Hoffmann et al., 2000). In one system (Neumann et al., 1999), eight plasmids encoding the eight influenza viral RNA segments under the control of the RNA polymerase I (PolI) promoter and terminator sequences are transfected into eukaryotic cells together with four RNA polymerase II (PolII)-driven plasmids for the expression of the three viral polymerase subunits and the nucleoprotein NP; these four proteins are required to initiate viral replication and transcription. An alternative system has also been developed (Hoffmann et al., 2000) that relies on eight plasmids in which the viral cDNAs are flanked by an RNA polymerase I promoter on one site and an RNA polymerase II promoter on the other site, which permits the vRNA and mRNA to be derived from the same template. These systems have allowed 6+2 reassortants to be engineered without the need for reassortment and screening procedures.

A limited number of mammalian cell lines are available for the production of influenza virus vaccines. They include Madin-Darby canine kidney (MDCK) (Brands et al., 1999; Palache et al., 1999; Halperin et al., 2002) and African green monkey kidney (Vero) (Kistner et al., 1998; Kistner et al., 1999a; Kistner et al., 1999b; Bruhl et al., 2000) cells. These cell lines cannot be transfected with high efficiencies, which sometimes limits their use in reverse genetics systems for influenza virus vaccine production; however, the generation of influenza virus in Vero cells has been demonstrated (Fodor et al., 1999; Nicolson et al., 2005).

Thus, what is needed is an improved method to prepare influenza virus.

SUMMARY OF THE INVENTION

The present invention provides isolated vectors (polynucleotides) which include tandem transcription units (transcription cassettes) including (i) RNA polymerase I (PolI) based transcription cassettes, and/or (ii) RNA polymerase II (PolII) based transcription cassettes, and/or (iii) RNA PolI/II based transcription cassettes on one or more vectors, e.g., plasmids or other, e.g., linear, nucleic acid delivery vehicles. In particular, the invention provides plasmids useful in a composition to prepare infectious negative strand segmented RNA viruses, which compositions have less than eight plasmids containing viral genes for virus production. For example, the compositions of the invention may include one, two, three, four, five, six, or seven plasmids having influenza virus genes, which composition, once introduced to a cell, yields infectious influenza virus. Thus, in one embodiment, to provide a reverse genetics system that reduces the number of plasmids for virus generation, up to eight RNA polymerase I transcription cassettes for the synthesis of the respective influenza virus RNAs were combined on one plasmid, and up to three transcription cassettes for three influenza virus polymerase subunits on one plasmid. As described hereinbelow, this approach allowed the efficient and robust generation of influenza A virus in Vero cells.

For instance, the invention includes a vector such as a plasmid including tandem transcription cassettes such as one or more of the following cassettes (i) a RNA PolI promoter, a cDNA for an influenza viral RNA (in negative- or positive-sense orientation), and a RNA PolI terminator; (ii) a RNA PolII promoter, a DNA for influenza virus PB2, PB1, PA, and/or NP protein, and a polyadenylation signal (RNA PolII transcription termination sequence), and/or (iii) a RNA PolII promoter, a RNA PolI transcription termination sequence, a cDNA for an influenza viral RNA (in positive-sense orientation), a RNA polymerase PolI promoter, and a RNA PolII transcription termination sequence. In cell lines that can be transfected efficiently, these approaches yielded up to $10^8$ viruses per mL of supernatant derived from transfected cells.

The combinations of transcription cassettes and/or vectors described herein are useful for the generation of live attenuated influenza vaccine virus, e.g., employing so-called "internal genes" (i.e., PB2, PB1, PA, NP, M, and NS) combined with HA and NA genes derived from currently circulating viruses. For instance, H5N1 viruses cannot be grown in eggs and so transcription cassettes containing those genes are particularly useful for the generation of H5N1 vaccine viruses. In one embodiment, the HA in a transcription cassette is a type A HA. In another embodiment, the HA in a transcription cassette is a type B HA. In yet another embodiment, genes from influenza virus type C are employed. In one embodiment, the RNA PolI promoter is a human RNA PolI promoter. In one embodiment, the NA cDNA further comprises NB sequences. In one embodiment, the composition further includes a transcription cassette comprising a PolI promoter operably linked to an influenza virus BM2 cDNA linked to a PolI transcription termination sequence.

In one embodiment, by combining all eight RNA PolI transcription cassettes for the generation of influenza virus on one plasmid, virus can be generated from five plasmids, i.e., one for the synthesis of all eight vRNAs and four for the synthesis of the polymerase proteins and NP proteins. In another embodiment, by combining four RNA PolII transcription cassettes for the synthesis of the polymerase and NP proteins on one plasmid, virus can be generated from two plasmids, i.e., one for the synthesis of all eight vRNAs and one for the synthesis of the polymerase proteins and NP proteins. In a further embodiment, by combining three RNA PolII transcription cassettes for the synthesis of the polymerase proteins on one plasmid, one RNA PolII transcription cassette for NP protein on one plasmid, and a plasmid for the synthesis of all eight vRNAs, virus may be generated from three plasmids. In another embodiment, by combining four RNA PolI transcription cassettes for the generation of HA, NA, M, and NS vRNAs and four RNA PolI/II transcription cassettes for the generation of PB2, PB1, PA and NP vRNAs and mRNAs on one plasmid, influenza virus can be generated from one plasmid.

Any suitable promoter or transcription termination sequence may be employed to express a protein, e.g., a viral protein, a protein of a nonviral pathogen, or a therapeutic protein, or a vRNA. Thus, in one embodiment, the invention provides isolated and purified vectors, e.g., plasmids, which express or encode influenza virus proteins, or express or encode influenza vRNA, both native and recombinant vRNA. Preferably, the promoter is suitable for expression in a particular host cell, e.g., avian or mammalian host cells such as canine, feline, equine, bovine, ovine, or primate cells including human cells, or preferably, for expression in more than one host.

In one embodiment, one or more vectors for vRNA production comprise a promoter including, but not limited to, a RNA PolI promoter, e.g., a human RNA PolI promoter, a RNA PolII promoter, a RNA PolIII promoter, a T7 promoter, or a T3 promoter. For a vector for vRNA which includes a RNA PolII promoter, the vector may optionally include ribozyme sequences (see PCT/US04/016649, the disclosure of which is incorporated by reference herein). Preferred transcription termination sequences for the vRNA vectors include, but are not limited to, a RNA PolI transcription termination sequence, a RNA PolII transcription termination sequence, or a ribozyme. Each RNA PolI promoter in a plasmid or a combination of plasmids to be employed together, may be the same or different. Each RNA PolI promoter in a plasmid or a combination of plasmids to be employed together, may be the same or different. Likewise, each RNA PolII transcription termination sequence in a plasmid or a combination of plasmids to be employed together, may be the same or different. Further, each RNA PolI transcription termination sequence in a plasmid or a combination of plasmids to be employed together, may be the same or different. The use of less than 12 plasmids, e.g., less than 10 plasmids, can yield titers of from $10^2$ TCID$_{50}$/mL, $10^3$ TCID$_{50}$/mL, $10^4$ TCID$_{50}$/mL, $10^5$ TCID$_{50}$/mL, $10^6$ TCID$_{50}$/mL, $10^7$ TCID$_{50}$/mL, $10^8$ TCID$_{50}$/mL, or more.

In one embodiment, cDNAs for one or more, e.g., two, three, four, five, six, seven or eight viral segments, are each flanked by RNA PolI termination and promoter sequences, and this transcription cassette is then flanked by an RNA PolII promoter and a RNA PolII polyadenylation signal (exemplified for the NP gene in FIG. 4). This approach yields both vRNA (synthesized by RNA PolI) and mRNA (synthesized by RNA PolII) from the same template. Additional plasmids for the synthesis of viral proteins are thus no longer required, reducing the number of transcription cassettes necessary for influenza virus production. The RNA PolI promoter and/or RNA PolI transcription termination sequence and/or the RNA PolII promoter and/or RNA PolII termination sequence in each vRNA/protein encoding cassette, may be the same or different as any other cassette.

In yet another embodiment, the invention includes the combination of two plasmids, one for the generation of HA vRNA and NA vRNA, and one for the generation of M vRNA and NS vRNA, and one plasmid containing four RNA PolI/II transcription cassettes (for the synthesis of PB2, PB1, PA, and NP vRNAs and mRNAs), allowing for virus generation from three plasmids, or one plasmid for PB2, PB1, PA, NP, M and NS vRNAs, one plasmid for HA vRNA, one plasmid for NA vRNA, and one plasmid for the synthesis of the polymerase and NP proteins, allowing virus generation from four plasmids. In another embodiment, the invention includes one plasmid for the generation of six vRNAs, e.g., PB2, PB1, PA, NP, M and NS vRNAs, one plasmid for the generation of two vRNAs, e.g., HA and NA vRNAs, and four plasmids each for the production of protein for PB2, PB1, PA, and NP, allowing for virus generation from six plasmids. In a further embodiment, the invention includes one plasmid for the generation of six vRNAs, e.g., PB2, PB1, PA, NP, M and NS vRNAs, one plasmid for the generation of two vRNAs, e.g., HA and NA vRNAs, and one plasmid for the production of protein for PB2, PB1, and PA, and one plasmid for the production of protein for NP, allowing for virus generation from four plasmids.

Other vectors useful in the compositions and/or methods of the invention include a DNA of interest, e.g., a gene or open reading frame (coding region) of interest for a prophylactic or therapeutic protein, flanked by viral sequences and optionally a PolI promoter and a PolI transcription termination sequence and/or a PolII promoter and a PolII transcription termination sequence. The DNA of interest may be in the positive sense or negative sense orientation relative to the promoter. The DNA of interest, whether in a vector for vRNA or protein production, may encode an immunogenic epitope, such as an epitope useful in a cancer therapy or vaccine, or gene therapy. In one embodiment, the DNA of interest is full-length influenza virus cDNA or an influenza virus DNA coding region, e.g., influenza A (e.g., any influenza A gene including any of the 15 HA or 9 NA subtypes), B or C DNA (see Chapters 45 and 46 of Fields Virology (Fields et al. (eds.), Lippincott-Raven Publ., Philadelphia, Pa. (1996), which are specifically incorporated by reference herein), although it is envisioned that the gene(s) from any source, e.g., from any virus, may be employed in the vectors or methods of the invention. The compositions of the invention may thus also include a transcription cassette comprising a promoter linked to 5' influenza virus sequences comprising 5' influenza virus noncoding sequences linked to a heterologous DNA of interest, i.e., one that is not found linked to influenza sequences in nature or in a different linkage than is found in nature, linked to 3' influenza virus sequences comprising 3' influenza virus noncoding sequences linked to a transcription termination sequence. In one embodiment, the DNA of interest is operably linked to a RNA polymerase promoter and a RNA polymerase transcription termination sequence.

In one embodiment, the DNA of interest comprises an open reading frame encoding an immunogenic polypeptide or peptide of a pathogen or a therapeutic polypeptide or peptide. In one embodiment, the DNA of interest is operably linked to a PolI promoter and a PolI transcription termination sequence while in another embodiment the DNA of interest is operably linked to a PolII promoter and a PolII transcription termination sequence. In yet another embodiment, the DNA of interest is operably linked to a PolI promoter and a PolI transcription termination sequence and to a PolII promoter and a PolII transcription termination sequence. The transcription cassette comprising the DNA of interest may be on the same plasmid as at least one other transcription cassette or may be on a different plasmid than the other transcription cassettes. When preparing virus, the DNA of interest may substitute for an influenza virus open reading frame or a portion thereof, or may be in addition to all influenza virus open reading frames.

The invention also provides a method to prepare virus, e.g., influenza virus, or deliver a gene by introducing a heterologous DNA of interest to an influenza virus vector. For example, the method includes contacting a cell with a plurality of the transcription cassettes of the invention, e.g., sequentially or simultaneously, for example, employing a composition of the invention, in an amount effective to yield infectious influenza virus. The invention also includes isolating virus from a cell contacted with the composition. Thus, the invention further provides isolated virus, as well as a host cell contacted with the composition or virus of the invention. In another embodiment, the invention includes contacting the cell with one or more vectors, either vRNA or protein production vectors, prior to other vectors, either vRNA or protein production vectors.

The methods of the invention allow easy manipulation of negative strand viruses such as influenza viruses, e.g., by the introduction of attenuating mutations into the viral genome. Further, because influenza viruses induce strong humoral and cellular immunity, the invention greatly enhances these viruses as vaccine vectors, particularly in view of the availability of natural variants of the virus, which may be employed sequentially, allowing repetitive use for gene therapy.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides a method to immunize an individual against a pathogen, e.g., a bacteria, virus, or parasite, or a malignant tumor. The method comprises administering to the individual an amount of at least one isolated virus of the invention, optionally in combination with an adjuvant, effective to immunize the individual. The virus comprises vRNA comprising a sequence for a polypeptide encoded by the pathogen or a tumor-specific polypeptide.

Also provided is a method to augment or increase the expression of an endogenous protein in a mammal having an indication or disease characterized by a decreased amount or a lack of the endogenous protein. The method comprises administering to the mammal an amount of an isolated virus of the invention effective to augment or increase the amount of the endogenous protein in the mammal. The virus comprises vRNA for a polypeptide which augments or increases the amount of the endogenous protein. Preferably, the mammal is a human.

DETAILED DESCRIPTION OF THE INVENTION

Definitions

Figure 1:
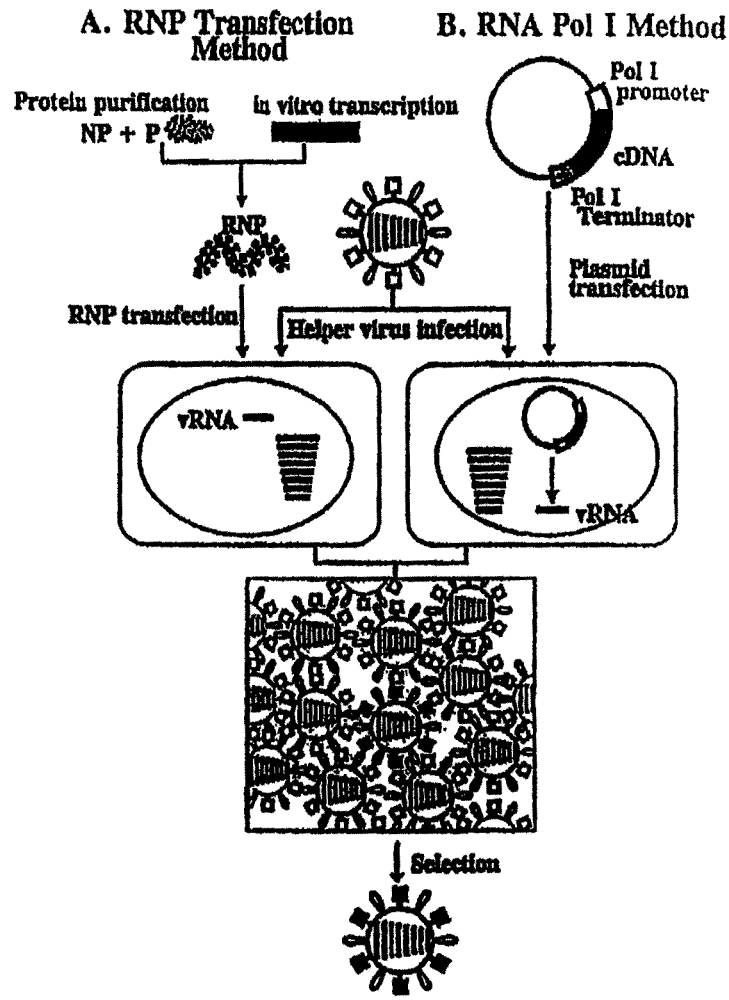
FIG. 1. Schematic diagram of established reverse genetics systems. In the RNP transfection method (A), purified NP and polymerase proteins are assembled into RNPs with use of in vitro-synthesized vRNA. Cells are transfected with RNPs, followed by helper virus infection. In the RNA polymerase I method (B), a plasmid containing the RNA polymerase I promoter, a cDNA encoding the vRNA to be rescued, and the RNA polymerase I terminator is transfected into cells. Intracellular transcription by RNA polymerase I yields synthetic vRNA, which is packaged into progeny virus particles upon infection with helper virus. In A) and B), transfectant viruses (i.e., those containing RNA derived from cloned cDNA), are selected from the helper virus population. In the method shown in (C), plasmids containing the RNA polymerase I promoter a cDNA for each of the eight viral RNA segments, and the RNA polymerase I terminator are transfected into cells together with protein expression plasmids. Although infectious viruses can be generated with plasmids expressing PA, PB1, PB2, and NP, expression of all remaining structural proteins (shown in brackets) increases the efficiency of virus production depending on the virus generated.
Figure 2:
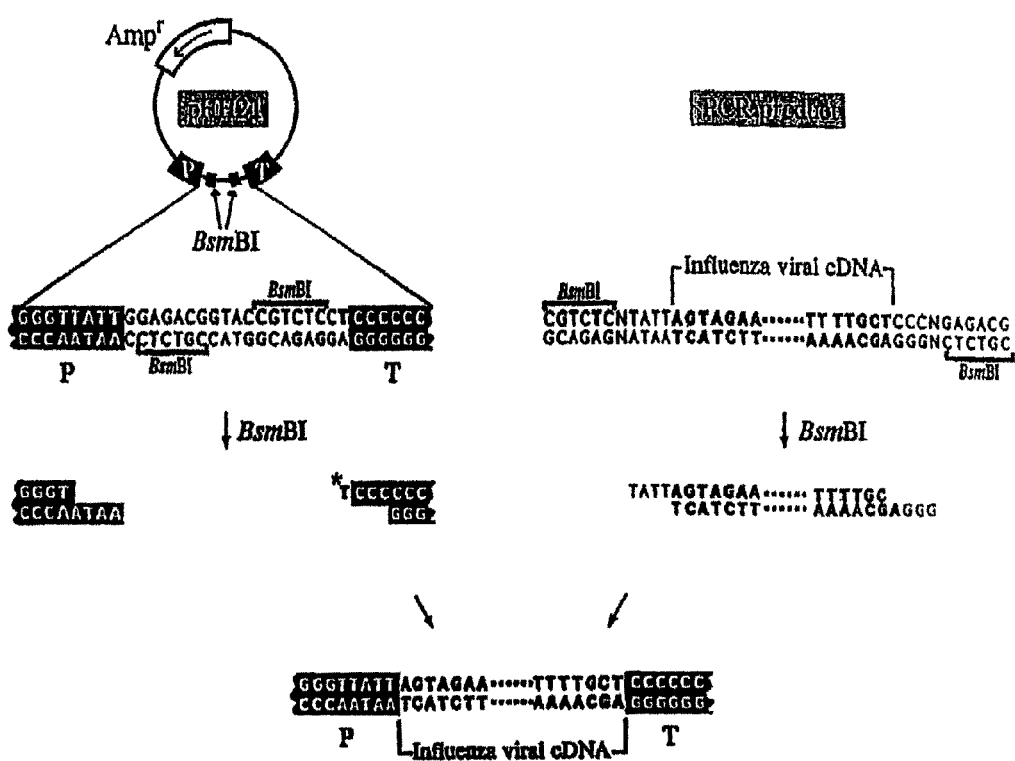
FIG. 2. Schematic diagram of the generation of RNA polymerase I constructs (SEQ ID NOs:1-12). cDNAs derived from influenza virus were amplified by PCR, digested with BsmBI and cloned into the BsmBI sites of the pHH21 vector (E. Hoffmann, Ph.D. thesis, Justus, Liebig-University, Giessen, Germany), which contains the human RNA polymerase I promoter (P) and the mouse RNA polymerase I terminator (T). The thymidine nucleotide upstream of the terminator sequence (*T) represents the 3' end of the influenza viral RNA. Influenza A virus sequences are shown in bold face letters.

As used herein, the terms "isolated and/or purified" refer to in vitro preparation, isolation and/or purification of a nucleic acid molecule such as a plasmid of the invention or a virus of the invention, so that it is not associated with in vivo substances, or is substantially purified from in vitro substances. An isolated virus preparation is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques, to introduce changes to the viral genome, or otherwise artificially generated. As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

A "highly transfectable cell" as used herein is a cell where transfection efficiencies with a single plasmid reach about 95%, e.g., as measured by protein expression in transfected cells and/or where transfection with more than 5 plasmids with influenza viral genes for virus production of a nonattenuated influenza virus, yields a virus titer of at least about $10^6$ $TCID_{50}$/mL by day 2 post-transfection or of an attenuated virus yields a virus titer of about $10^2$ $TCID_{50}$/mL. Exemplary highly transfectable cells include but are not limited to 293T cells. In contrast, a "cell with reduced transfection efficiency" as used herein is a cell wherein transfection efficiencies with a single plasmid are less than about 50% and/or where transfection with more than 5 plasmids with influenza viral genes for virus production of a nonattenuated influenza virus, yields a virus titer of less than about $3\times10^5$ $TCID_{50}$/mL by 2 days after transfection. Exemplary cells with reduced transfection efficiency include but are not limited to Vero cells and MDCK cells.

Negative-Sense RNA Viruses

Negative-sense RNA viruses are classified into seven families (Rhabdoviridae, Paramyxoviridae, Filoviridae, Bornaviridae, Orthomyxoviridae, Bunyaviridae, and Arenaviridae) which include common human pathogens, such as respiratory syncytial virus, influenza virus, measles virus, and Ebola virus, as well as animal viruses with major economic impact on the poultry and cattle industries (e.g., Newcastle disease virus and Rinderpest virus). The first four families are characterized by nonsegmented genomes, while the latter three have genomes comprised of six-to-eight, three, or two negative-sense RNA segments, respectively. The common feature of negative-sense RNA viruses is the negative polarity of their RNA genome; i.e., the viral RNA (vRNA) is complementary to mRNA and therefore is not infectious by itself. In order to initiate viral transcription and replication, the vRNA has to be transcribed into a plus-sense mRNA or cRNA, respectively, by the viral polymerase complex and the nucleoprotein; for influenza A viruses, the viral polymerase complex is comprised of the three polymerase proteins PB2, PB1, and PA. During viral replication, cRNA serves as a template for the synthesis of new vRNA molecules. For all negative-stranded RNA viruses, non-coding regions at both the 5' and 3' termini of the vRNA and cRNA are critical for transcription and replication of the viral genome. Unlike cellular or viral mRNA transcripts, both cRNA and vRNA are neither capped at the 5' end nor polyadenylated at the very 3' end.

The basic functions of many viral proteins have been elucidated biochemically and/or in the context of viral infection. However, reverse genetics systems have dramatically increased our knowledge of negative-stranded segmented and non-segmented RNA viruses with respect to their viral replication and pathogenicity, as well as to the development of live attenuated virus vaccines. Reverse genetics, as the term is used in molecular virology, is defined as the generation of virus possessing a genome derived from cloned cDNAs (for a review, see Neumann et al., 2002).

Influenza Virus

Influenza A viruses possess a genome of eight single-stranded negative-sense viral RNAs (vRNAs) that encode a total of ten to eleven proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, the M segment of influenza B virus encodes two proteins, M1 and BM2, through a termination-reinitiation scheme of tandem cistrons, and the NA segment encodes the NA and NB proteins from a bicistronic mRNA. Influenza C virus, which has 7 vRNA segments, relies on spliced transcripts to produce M1 protein; the product of the unspliced mRNA is proteolytically cleaved to yield the CM2 protein. In addition, influenza C virus encodes a HA-esterase rather than individual HA and NA proteins.

Thogotovirus

Thogotoviruses (THOV) represent a new genus in the family of Orthomyxoviridae. They are transmitted by ticks and have been found in domestic animals, including camels, goats, and cattle. Consequently, THOV can replicate in tick and vertebrate cells. The THOV genome comprises six segments of single-stranded, negative-sense RNA. The proteins encoded by the three largest segments show significant homology to the influenza virus polymerase proteins PB2, PB1, and PA. Segment 5 encodes a protein related to influenza virus NP. The THOV glycoprotein, which is encoded by segment 4, is not homologous to either influenza virus HA or NA, but it shows sequence similarity to the Baculovirus glycoprotein. The smallest segment is thought to encode a matrix protein and does not resemble any of the influenza virus proteins. Like influenza virus, both the 3' and 5' ends of the vRNA are required for promoter activity, and this activity is located in the terminal 14 and 15 nucleotides of the 3' and 5' ends of the vRNA, respectively.

The mRNA synthesis of THOV is primed by host cell-derived cap structures. However, in contrast to influenza virus, only the cap structures (without additional nucleotides) are cleaved from cellular mRNAs (Albo et al., 1996; Leahy et al., 1997; Weber et al., 1996). In vitro cleavage assays revealed that both the 5' and 3' ends of vRNA are required for endonuclease activity (Leahy et al., 1998), but addition of a model cRNA promoter does not stimulate endonuclease activity (Leahy et al., 1998), as has been shown for influenza virus (Hagen et al., 1994). A 'hook' structure has been proposed for THOV (Leahy et al., 1997; Weber et al., 1997), which is similar to the corkscrew structure proposed for influenza virus. This 'hook' structure, however, is only found in the THOV vRNA promoter. The cRNA promoter sequence does not allow the formation of base pairs between positions 2 and 9, and between 3 and 8 at the 5' end of the cRNA. Alterations at positions 3 or 8 to allow base-pairing between these nucleotides stimulates endonuclease activity, which is strong supporting evidence of the proposed 'hook' structure (Leahy et al., 1998). Moreover, this structure might be crucial for the regulation of the THOV life cycle; the vRNA promoter, forming the 'hook' structure, may stimulate PB2 endonuclease activity, thereby allowing transcription. The cRNA promoter, in contrast, may not form the 'hook' structure and may therefore be unable to stimulate endonuclease activity, thus resulting in replication.

Bunyaviridae

The family Bunyaviridae includes several viruses that cause hemorrhagic or encephalitic fevers in humans (e.g., Rift fever valley, Hantaan, La Crosse, and Crimean-Congo hemorrhagic fever). The spherical and enveloped virions contain three segments of single-stranded, negative-sense RNA (reviewed in Elliott, 1997). The largest segment (L) encodes the viral RNA polymerase protein (L protein), whereas the M segment encodes the two viral glycoproteins G1 and G2, and a nonstructural protein (NSm). The smallest segment (S) encodes the nucleocapsid protein (N) and a second nonstructural protein (NSs). Virus replication and transcription take place in the cytoplasm, and newly assembled virions bud through the membranes of the Golgi apparatus.

Bridgen & Elliott (1996) have established a reverse genetics system to generate infectious Bunyamwera virus entirely from cloned cDNAs. They followed a strategy first described by Schnell et al. (1994) for rabies virus: intracellular transcription of a cDNA coding for the positive-sense antigenomic RNA (but not for the negative-sense genomic RNA) in cells expressing the viral polymerase and nucleoprotein. Bridgen & Elliott (1996) infected HeLaT4+ cells with vaccinia virus expressing T7 polymerase and transfected these cells with plasmids expressing proteins encoded by the S, M, and L segments. They then transfected these cells with three plasmids encoding full-length anti-genomic cDNAs flanked by the T7 polymerase promoter and the hepatitis delta virus ribozyme. To increase the number of bunyavirus particles relative to the number of vaccinia virus particles, the authors used mosquito cells in which Bunyamwera but not Vaccinia virus replicates. This protocol can be used not only to genetically engineer Bunyaviridae, but also generate reassortant viruses that cannot easily be obtained by coinfecting cells with different Bunyaviridae strains.

To study bunyavirus promoter elements and the viral proteins that are required for transcription and replication, Dunn et al. (1995) cloned the CAT gene in the negative-sense orientation between the 5' and 3' nontranslated regions of the Bunyamwera S RNA segment. Cells were transfected with constructs expressing the proteins encoded by the L and S segment and were then transfected with in vitro transcribed RNA, which resulted in CAT activity. The bunyavirus S segment encodes two proteins, N and NSs, in overlapping reading frames. To determine whether both of these proteins are required for transcription and replication, constructs expressing only N or NSs were tested for CAT activity. N protein expression, together with L protein, resulted in CAT activity, whereas no CAT activity was detected with the NSs expression construct. Thus, the L and N proteins are sufficient for transcription and replication of a bunyavirus-like RNA.

As with influenza virus, the terminal sequences of bunyavirus RNAs are complementary and highly conserved. It has therefore been assumed that these sequence elements define the bunyaviral promoter and are crucial for promoter activity. Deletion of five nucleotides at the 3' end of the viral RNA drastically reduces CAT expression (Dunn et al., 1995). In contrast, addition of two nucleotides at the 5' end, or of 11 or 35 nucleotides at the 3' end does not abolish CAT expression (Dunn et al., 1995). Therefore, like the influenza virus polymerase complex, the bunyavirus polymerase protein can apparently start transcription and/or replication internally.

Recombinant Influenza Virus Vectors of the Invention

The use of vectors described herein significantly reduces the number of plasmids required for the generation of segmented virus such as influenza virus, increases the rescue efficiency of influenza virus in cell lines that can be transfected with high efficiencies, allowing the generation of viruses that are severely attenuated, and/or allows the generation of influenza virus in cell lines that cannot be transfected with high efficiencies, including cell lines for the production of human vaccines (e.g., Vero cells). Accordingly, the use of the vectors of the invention reduces the number of variables for virus generation, resulting in more consistent generation of influenza virus, and decreasing the burden of providing proper documentation of plasmid history, purity, and toxicity.

These advantages allow the speedy generation of vaccine viruses, especially for pandemics. Moreover, the invention disclosed herein is not limited to influenza virus but can be applied to any other antisense RNA virus, e.g., Paramyxoviridae, Rhabdoviridae, Filoviridae, Reoviridae, Arenaviridae or Bunyaviridae.

The invention provides at least one of the following isolated and/or purified vectors or a composition which includes one or more vectors and/or two or more transcription cassettes: a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, a transcription cassette comprising a PolI promoter and a PolI transcription termination sequence and a PolII promoter and a PolII transcription termination sequence each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a DNA segment for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA.

A vector of the invention may include two or more transcription cassettes selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence.

In one embodiment, a vector of the invention includes two or more transcription cassettes selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and a transcription cassette comprising a PolII promoter operably linked to a DNA coding region for influenza virus NP linked to a PolII transcription termination sequence.

In another embodiment, a vector of the invention includes at least two transcription cassettes selected from a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus cDNA for NA, a full-length influenza virus NA cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and/or a transcription cassette comprising a PolI promoter operably linked to an influenza virus NS cDNA, e.g., a full-length influenza virus NS cDNA, linked to a PolI transcription termination sequence.

The invention further includes a vector with at least two transcription cassettes selected from a transcription cassette comprising a PolI promoter and a PolI transcription termination sequence and a PolII promoter and a PolII transcription termination sequence each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a DNA segment for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA.

Further provided is a vector which includes two or more transcription cassettes selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, a full-length influenza virus PB2 cDNA, linked to a PolI transcription termination sequence, a transcription cassette comprising a PolI promoter operably linked to an influenza virus HEF cDNA, e.g., a full-length influenza virus HEF cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a PolI promoter operably linked to an influenza virus M cDNA, e.g., a full-length influenza virus M cDNA, linked to a PolI transcription termination sequence, and/or a transcription cassette comprising a promoter operably linked to an influenza virus NS cDNA, e.g., a full-length influenza virus NS cDNA, linked to a PolI transcription termination sequence.

Also provided is a vector which includes two or more transcription cassettes selected from a transcription cassette comprising a PolI promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, and a transcription cassette comprising a PolI promoter operably linked to an influenza virus HEF cDNA, e.g., a full-length influenza virus HEF cDNA, linked to a PolI transcription termination sequence.

In one embodiment, the invention provides an isolated and/or purified vector which includes one or more transcription cassettes including a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HEF cDNA, e.g., a full-length influenza virus HEF cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, a transcription cassette comprising a PolI promoter and a PolI transcription termination sequence and a PolII promoter and a PolII transcription termination sequence each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a DNA segment for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA.

Exemplary Compositions of the Invention

The invention provides a composition comprising at least one plasmid which includes two or more transcription cassettes for vRNA production selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and/or a transcription cassette comprising a PolI promoter operably linked to an influenza virus NS cDNA, e.g., a full-length influenza virus NS cDNA, linked to a PolI transcription termination sequence; and at least one plasmid which includes one or more transcription cassettes for mRNA production selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence. In one embodiment, each PolI promoter is the same. In one embodiment, each PolII promoter is the same. In one embodiment, each PolI transcription terminator sequence is the same. In one embodiment, each PolII transcription terminator sequence is the same.

In one embodiment, at least one plasmid for vRNA production includes transcription cassettes for influenza virus PA, influenza virus PB1, influenza virus PB2, influenza virus HA, influenza virus NP, influenza virus NA, influenza virus M, and influenza virus NS segments. In one embodiment, the at least one plasmid for mRNA production includes two or more transcription cassettes for influenza virus PA, influenza virus PB1, influenza virus PB2 or influenza virus NP, e.g., the at least one plasmid for mRNA production includes cassettes for influenza virus PA, influenza virus PB1, influenza virus PB2 and influenza virus NP. In one embodiment, the at least one plasmid for mRNA production includes three of the cassettes, wherein the composition further comprises a third plasmid for mRNA production with a PolII promoter operably linked to a DNA coding region for an influenza virus gene linked to a PolII transcription termination sequence, wherein the DNA coding region in the third plasmid is for an influenza virus gene that is not on the plasmid which includes the three cassettes, for instance, the at least one plasmid for mRNA production includes cassettes for influenza virus PA, influenza virus PB1, influenza virus PB2 and the third plasmid includes a cassette for influenza virus NP. In another embodiment, the at least one plasmid for vRNA production includes transcription cassettes for influenza virus PA, influenza virus PB1, influenza virus PB2, influenza virus NP, influenza virus M, and influenza virus NS. Also included is a plasmid for vRNA production which includes a transcription cassette comprising a PolI promoter operably linked to an influenza virus HA cDNA, e.g., a full-length influenza virus HA cDNA, linked to a PolI transcription termination sequence and a transcription cassette comprising a PolI promoter operably linked to an influenza virus NA cDNA, e.g., a full-length influenza virus NA cDNA, linked to a PolI transcription termination sequence, for instance, the at least one plasmid for mRNA production includes cassettes for influenza virus PA, influenza virus PB1, influenza virus PB2 and influenza virus NP. In another embodiment, the at least one plasmid for mRNA production includes three of the cassettes, wherein the composition further comprises a third plasmid for mRNA production with a PolII promoter operably linked to a DNA coding region for an influenza virus gene linked to a PolII transcription termination sequence, wherein the DNA coding region in the third plasmid is for an influenza virus gene that is not on the plasmid which includes the three cassettes, e.g., the at least one plasmid for mRNA production includes cassettes for influenza virus PA, influenza virus PB1, influenza virus PB2 and the third plasmid includes a cassette for influenza virus NP.

In one embodiment, a composition of the invention comprises a plasmid which includes a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and a transcription cassette comprising a PolI promoter operably linked to an influenza virus NS cDNA, e.g., a full-length influenza virus NS cDNA, linked to a PolI transcription termination sequence. In one embodiment, the HA in a transcription cassette is a type A HA. In another embodiment, the HA in a transcription cassette is a type B HA. In one embodiment, the RNA polymerase I promoter is a human RNA polymerase I promoter. In one embodiment, the NA segment in a transcription cassette is a type B NA segment, i.e., one for both the influenza B virus NA and NB proteins. In one embodiment, the composition further includes a transcription cassette comprising a PolI promoter operably linked to an influenza virus M cDNA, e.g., one for both M1 and BM2, linked to a PolI transcription termination sequence.

Also provided a composition comprising a plasmid which includes two or more transcription cassettes selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence.

In another embodiment, the invention provides a composition comprising a plasmid which includes one or more transcription cassettes selected from a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus cDNA for NA, e.g., a full-length influenza virus NA cDNA, linked to a PolI transcription termination sequence, a transcription cassette comprising a PolI promoter operably linked to an influenza virus M cDNA, e.g., a full-length influenza virus M cDNA, influenza virus linked to a PolI transcription termination sequence, and a transcription cassette comprising a PolI promoter operably linked to an influenza virus NS cDNA, e.g., a full-length influenza virus NS cDNA, linked to a PolI transcription termination sequence; and one or more transcription cassettes selected from a transcription cassette comprising a PolI promoter and a PolI transcription termination sequence and a PolII promoter and a PolII transcription termination sequence each operably linked to a cDNA for influenza virus PA, e.g., a full-length influenza virus PA cDNA, a transcription cassette comprising a PolI promoter and a PolI transcription termination sequence and a PolII promoter and PolII transcription termination sequence each operably linked to a cDNA for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a cDNA for influenza virus PB2, e.g., a full-length influenza virus PB2 cDNA, and a transcription cassette comprising a PolI promoter and a PolI transcription termination sequence and a PolII promoter and a PolII transcription termination sequence each operably linked to a cDNA for influenza virus NP, e.g., a full-length influenza virus NP cDNA. In one embodiment, the HA in a transcription cassette is a type A HA. In another embodiment, the HA in a transcription cassette is a type B HA. In one embodiment, the RNA PolI promoter is a human RNA PolI promoter. In one embodiment, the NA cDNA in a transcription cassette is a type B NA cDNA, i.e., one having NA and NB. In one embodiment, the composition further includes a transcription cassette comprising a PolI promoter operably linked to an influenza virus M cDNA, e.g., one having M1 and BM2, linked to a PolI transcription termination sequence.

Further provided is a composition comprising a plasmid which includes a transcription cassette comprising a PolI promoter and a PolI transcription termination sequence and a PolII promoter and a PolII transcription termination sequence each operably linked to a cDNA for influenza virus PA, e.g., a full-length influenza virus PA, a transcription cassette comprising a PolI promoter and a PolI transcription termination sequence and a PolII promoter and PolII transcription termination sequence each operably linked to a cDNA for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a cDNA for influenza virus PB2, e.g., a full-length influenza virus PB2 cDNA, and a transcription cassette comprising a PolI promoter and a PolI transcription termination sequence and a PolII promoter and a PolII transcription termination sequence each operably linked to a cDNA for influenza virus NP, e.g., a full-length influenza virus NP cDNA.

Also included is a composition comprising at least one plasmid for vRNA production which includes two or more transcription cassettes selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HEF cDNA, e.g., a full-length influenza virus HEF cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and/or a transcription cassette comprising a promoter operably linked to an influenza virus NS cDNA, e.g., a full-length influenza virus NS cDNA, linked to a PolI transcription termination sequence; and at least one plasmid for mRNA production which includes one or more transcription cassettes selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence.

In one embodiment, the at least one plasmid for vRNA production includes transcription cassettes for influenza virus PA, influenza virus PB1, influenza virus PB2, influenza virus HEF, influenza virus NP, influenza virus M, and influenza virus NS segments. In one embodiment, the at least one plasmid for mRNA production includes two or more transcription cassettes for influenza virus PA, influenza virus PB1, influenza virus PB2 or influenza virus NP, e.g., the at least one plasmid for mRNA production includes cassettes for influenza virus PA, influenza virus PB1, influenza virus PB2 and influenza virus NP. In one embodiment, the at least one plasmid for mRNA production includes three of the cassettes, wherein the composition further comprises a third plasmid for mRNA production with a PolII promoter operably linked to a DNA coding region for an influenza virus gene linked to a PolII transcription termination sequence, wherein the DNA coding region in the third plasmid is for an influenza virus gene that is not on the plasmid which includes the three cassettes, e.g., the at least one plasmid for mRNA production includes cassettes for influenza virus PA, influenza virus PB1, influenza virus PB2 and the third plasmid includes a cassette for influenza virus NP. In one embodiment, the at least one plasmid for vRNA production includes transcription cassettes for influenza virus PA, influenza virus PB1, influenza virus PB2, influenza virus NP, influenza virus M, and influenza virus NS segment. For instance, the composition includes a plasmid for vRNA production which includes a transcription cassette comprising a PolI promoter operably linked to an influenza virus HEF cDNA, e.g., a full-length influenza virus HEF cDNA, linked to a PolI transcription termination sequence.

Also provided is a composition comprising a plasmid which includes two or more transcription cassettes selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HEF cDNA, e.g., a full-length influenza virus HEF cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and/or a transcription cassette comprising a promoter operably linked to an influenza virus NS cDNA, e.g., a full-length influenza virus NS cDNA, linked to a PolI transcription termination sequence. In one embodiment, each transcription cassette for vRNA production is on one plasmid. In one embodiment, each transcription cassette for mRNA production is on one plasmid. In one embodiment, each transcription cassette is on one plasmid. In one embodiment, the RNA PolI promoter is a human RNA PolI promoter.

The invention also includes a composition comprising a plasmid which includes one or more transcription cassettes selected from a transcription cassette comprising a PolI promoter operably linked to an influenza virus HEF cDNA, e.g., a full-length influenza virus HEF cDNA, linked to a PolI transcription termination sequence, a PolI transcription cassette comprising a promoter operably linked to an influenza virus M cDNA, e.g., a full-length influenza virus M cDNA, linked to a PolI transcription termination sequence, and a transcription cassette comprising a PolI promoter operably linked to an influenza virus NS cDNA, e.g., a full-length influenza virus NS cDNA, linked to a PolI transcription termination sequence; and one or more transcription cassettes selected from a transcription cassette comprising a PolI promoter and a PolI transcription termination sequence and a PolII promoter and a PolII transcription termination sequence each operably linked to a cDNA for influenza virus PA, e.g., a full-length influenza virus PA cDNA, a transcription cassette comprising a PolI promoter and a PolI transcription termination sequence and a PolII promoter and a PolII transcription termination sequence each operably linked to a cDNA for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a cDNA for influenza virus PB2, e.g., a full-length influenza virus PB2 cDNA, and a transcription cassette comprising a PolI promoter and a PolI transcription termination sequence and a PolII promoter and/or a PolII transcription termination sequence each operably linked to a cDNA for influenza virus NP, e.g., a full-length influenza virus NP cDNA. In one embodiment, each transcription cassette for vRNA production is on one plasmid. In one embodiment, each transcription cassette for mRNA production is on one plasmid. In one embodiment, each transcription cassette is on one plasmid. In one embodiment, the RNA PolI promoter is a human RNA PolI promoter.

In one embodiment, the composition when contacted with a cell which is optionally a 293T cell or a Vero cell, yields detectable amounts of influenza virus, e.g., a titer of at least $10^2$ to at least $10^3$ $TCID_{50}$/mL.

Exemplary Methods

The invention also provides a method to prepare influenza virus. The method includes contacting a cell with a plasmid which includes two or more transcription cassettes selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, and/or a transcription cassette comprising a PolI promoter operably linked to an influenza virus M cDNA, e.g., a full-length influenza virus M cDNA, linked to a PolI transcription termination sequence and/or a transcription cassette comprising a PolI promoter operably linked to an influenza virus NS cDNA, e.g., a full-length influenza virus NS cDNA, linked to a PolI transcription termination sequence; and a plasmid which includes one or more transcription cassettes selected from a transcription cassette, a transcription cassette comprising a PolII promoter operably linked to a DNA coding region for influenza virus PA, a transcription cassette comprising a PolII promoter operably linked to a DNA coding region for influenza virus PB1, a transcription cassette comprising a PolII promoter operably linked to a DNA coding region for influenza virus PB2, and/or a transcription cassette comprising a PolII promoter operably linked to a DNA coding region for influenza virus NP.

In one embodiment, a method to prepare influenza virus includes contacting a cell with a plasmid which includes a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, a transcription cassette comprising a promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, and optionally includes one or more transcription cassettes selected from a transcription cassette comprising a PolI promoter and a PolI transcription termination sequence and a PolII promoter and a PolII transcription termination sequence each operably linked to a cDNA for influenza virus PA, e.g., a full-length influenza virus PA cDNA, a transcription cassette comprising a PolI promoter and a PolI transcription termination sequence and a PolII promoter and a PolII transcription termination sequence each operably linked to a cDNA for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a cDNA for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a cDNA for influenza virus NP e.g., a full-length influenza virus NP cDNA.

In another embodiment, the invention provides a method to prepare influenza virus which includes contacting a cell with a plasmid which includes two or more transcription cassettes selected from a transcription cassette comprising a PolI promoter operably linked to an influenza virus PA cDNA e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a transcription termination sequence, a transcription cassette comprising a PolI promoter operably linked to an influenza virus HEF cDNA, e.g., a full-length influenza virus HEF cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA e.g., a full-length influenza virus M cDNA, linked to a PolI transcription termination sequence, and/or a transcription cassette comprising a PolI promoter operably linked to an influenza virus NS cDNA, e.g., a full-length influenza virus NS cDNA, linked to a PolI transcription termination sequence; and a plasmid which includes one or more transcription cassettes selected from a transcription cassette comprising a PolII promoter operably linked to a DNA coding region for influenza virus PA, a transcription cassette comprising a PolII promoter operably linked to a DNA coding region for influenza virus PB1, a transcription cassette comprising a PolII promoter operably linked to a DNA coding region for influenza virus PB2, and/or a transcription cassette comprising a PolII promoter operably linked to a DNA coding region for influenza virus NP.

Further provided is a method to prepare influenza virus. The method includes contacting a cell with a plasmid which includes a transcription cassette comprising a PolI promoter operably linked to an influenza virus HEF cDNA, e.g., a full-length influenza virus HEF cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, and optionally includes one or more transcription cassettes selected from a transcription cassette comprising a PolI promoter and a PolI transcription termination sequence and a PolII promoter and a PolII transcription termination sequence each operably linked to a cDNA for influenza virus PA, e.g., a full-length influenza virus PA cDNA, a transcription cassette comprising a PolI promoter and a PolI transcription termination sequence and a PolII promoter and a PolII transcription termination sequence each operably linked to a cDNA for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a cDNA for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a cDNA for influenza virus NP, e.g., a full-length influenza virus NP cDNA.

In one embodiment, the method of the invention includes contacting a cell with a vector comprising a transcription cassette comprising a promoter linked to 5' influenza virus sequences comprising 5' influenza virus noncoding sequences and optionally adjacent portions of the coding sequence (see PCT/US03/04233, which is incorporated by reference herein), linked to a DNA of interest linked to 3' influenza virus sequences comprising 3' influenza virus non-coding sequences and optionally adjacent portions of the coding sequence, linked to a transcription termination sequence (see PCT/US03/04233). In one embodiment, the DNA of interest is in the sense orientation. In another embodiment, the DNA of interest is in the negative sense orientation. The DNA of interest may include an open reading frame encoding an immunogenic polypeptide or peptide of a pathogen or a therapeutic polypeptide or peptide. The DNA of interest may be operably linked to a PolI promoter and a PolI transcription termination sequence, and/or the DNA of interest is operably linked to a PolII promoter and a PolII transcription termination sequence.

Cell Lines and Influenza Viruses that can be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The vaccine virus is preferably purified by a process that has been shown to give consistent results (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976; Webster et al., 1977); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines.

Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines.

Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reassorted virus according to known methods (see, e.g., Murphy, 1993). Since resistance to influenza A virus is mediated by the development of an immune response to the HA and NA glycoproteins, the genes coding for these surface antigens must come from the circulating wild-type strains. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, 1994; Murphy, 1993). Reassortant progeny are then selected at 25° C. (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced, for example, into the PB2 polymerase gene (Subbarao et al., 1993) or the NS gene. Thus, new donor viruses can also be generated bearing attenuating mutations introduced by site-directed mutagenesis, and such new donor viruses can be used in the production of live attenuated reassortant H1N1 and H3N2 vaccine candidates in a manner analogous to that described above for the A/AA/6/60 ca donor virus.

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; *Avery's Drug Treatment,* 1987; Osol, 1980. The composition of the invention is generally presented in the form of individual doses (unit doses).

Conventional vaccines generally contain about 0.1 to 200 μg, preferably 10 to 15 μg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Avery's, 1987; and Osol, 1980.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Berkow et al., 1992; and Avery, 1987. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease.

For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; and Avery, 1987.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Avery's, 1987; and Ebadi, 1985.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg, per component for older children 3 years of age, and 7.5 µg per component for older children <3 years of age. The quantity of NA can also be standardized, however, this glycoprotein can be labile during the processor purification and storage. Each 0.5-ml dose of vaccine preferably contains approximately 1-50 billion virus particles, and preferably 10 billion particles.

The invention will be further described by the following non-limiting examples.

EXAMPLE 1

The genome of influenza A or B virus is an 8-segmented single negative strand (C has only 7 segments). Two of the genes that are critical for virus infection, as well as for strategies to develop vaccines for influenza, are the hemagglutinin (HA) and neuraminidase (NA) genes. Entry into a host cell is facilitated by binding of the HA spikes to mucoproteins containing terminal N-acetyl neuraminic acid (sialic acid) groups. Classical influenza vaccines are usually made by melding the HA and NA genes, along with six other genes from a "harmless" master strain. This process is very time consuming and is often prone to low titers during vaccine development. A methodology that allows one to generate synthetic influenza virus by reverse genetics has been employed to prepare viruses, e.g., the recombinant virus contains HA and NA genes from pathogenic strains and 6 genes from a master strain are assembled. In particular, these cloned genes, along with proteins necessary for replication and transcription (polymerase PB2, PB1, PA, and NP), encoded in additional plasmids are transfected into cell lines. Live attenuated virus is then harvested for vaccine production.

Materials and Methods

Cells.

293T human embryonic kidney cells and African green monkey kidney (Vero) cells were maintained in DMEM supplemented with 10% FCS. For all experiments, Vero CCL-81 cells were used, which have been previously used to produce an inactivated Japanese encephalitis vaccine and have been screened for lack of tumorgenicity and adventitious infectious agents (Sugawara et al., 2002). Madin-Darby canine kidney (MDCK) cells were maintained in MEM containing 5% NCS. All cells were maintained at 37° C. in 5% $CO_2$.

Construction of Plasmids.

To combine RNA polymerase I transcription cassettes for the synthesis of the influenza viral RNA segments, transcription cassettes comprising the human RNA polymerase I promoter, an influenza viral cDNA in negative-sense orientation, and the mouse RNA polymerase I terminator (Neumann et al., 2002) were amplified by PCR with oligonucleotides that contained recognition sequences for restriction endonucleases that were not present in the viral genome. As templates, pPolI-WSN-PB2, -PB1, -PA, -HA, -NP, -NA, -M, -NS (all described in Neumann et al., 2002), which contained the respective viral cDNA of A/WSN/33 (H1N1) virus positioned between RNA polymerase I promoter and terminator sequences, were employed. PCR products were cloned into standard vectors that contained the respective restriction sites and were sequenced to confirm that they lacked unwanted mutations. The functionality of the resulting plasmids was confirmed by reverse genetics.

A modified pTM1 vector (Moss et al., 1990) with flanking, unique restriction sites was used to step-wise combine individual RNA polymerase I transcription cassettes (this vector is described in more detail below). At each cloning step, the functionality of the resulting plasmids, which contained 2-7

RNA polymerase I transcription units, was confirmed by reverse genetics. The final plasmid, pPolI-WSN-All (FIG. 3A), contained eight RNA polymerase I transcription cassettes for the synthesis of all eight influenza A/WSN/33 viral RNAs. This plasmid was stably maintained in E. coli JM109 cells at room temperature; bacterial cultures were grown in Terrific Broth medium for approximately 30 hours.

Using the same strategy, two plasmids (pTM-PolI-WSN-HA-NA and pTM-PolI-WSN-PB2-PB1-PA-NP-M-NS, respectively) were generated (FIG. 3B) that contained RNA polymerase I transcription cassettes for the HA and NA segments, and the remaining six viral segments (i.e., PB2, PB1, PA, NP, M, and NS), respectively.

Plasmids pCAWSPB2, pCAWSPB1, and pCAWSPA included the chicken β-actin promoter, the coding sequence of the A/WSN/33 PB2, PB1, or PA protein, and a polyadenylation signal. These RNA polymerase II transcription units were flanked by recognition sequences for unique restriction endonucleases, either by PCR or by inserting short DNA linkers. PCR-amplified transcription cassettes were sequenced in their entirety, before the three RNA polymerase II transcription cassettes were combined by using the unique restriction sites. The functionality of the resulting plasmid (pC-PolII-WSN-PB2-PB1-PA, FIG. 3C) was verified by reverse genetics.

Generation of Virus from Plasmids.

293T cells ($1 \therefore 10^6$) or Vero CCL-81 cells ($5 \times 10^5$) were transfected by using Trans IT-LT1 (Mirus, Madison, Wis.) according to the manufacturer's instructions. Briefly, transfection reagent (2 µl of Trans IT-LT1 per µg of DNA for the transfection of 293T cells; 4 µl of Trans IT-LT1 per µg of DNA for the transfection of Vero cells) was diluted in 100 µl of Opti-MEM (GIBCO BRL), incubated for 5 minutes at room temperature, and added to pre-mixed DNAs. For all transfection experiments, 0.1 µg of each of the 'single unit' plasmids for the synthesis of viral RNAs (i.e., pPolI-WSN-PB2, -PB1, -PA, -HA, -NP, -NA, -M, -NS; described in Neumann et al. (1999), 1 µg of plasmids containing more than one RNA polymerase I transcription unit (i.e., pTM-PolI-WSN-All, pTM-PolI-WSN-HA-NA, or pTM-PolI-WSN-PB2-PB1-PA-NP-M-NS), and 1 µg of each of the protein expression plasmids, were used. At the indicated times after transfection, the 50% tissue culture infectious dose ($TCID_{50}$) in MDCK cells was determined.

Results

Plasmids Containing Multiple RNA Polymerase I or II Transcription Cassettes.

To allow influenza virus generation from fewer than 8-12 plasmids (Neumann et al., 1999; Hoffmann et al., 2000; Fodor et al., 1999), RNA polymerase I transcription cassettes for viral RNA (vRNA) synthesis, or RNA polymerase II transcription cassettes for mRNA synthesis, were combined on one plasmid. As a model, the A/WSN/33 (WSN) virus, for which parameters and efficiencies of viral generation are well established, was used. Briefly, RNA polymerase I transcription cassettes comprising the human RNA polymerase I promoter, an influenza viral cDNA in negative-sense orientation, and the mouse RNA polymerase I terminator, were amplified by PCR, cloned and sequenced, and then joined step-wise by the use of unique restriction sites. As a vector backbone, a modified pTM1 vector (Moss et al., 1990) was used that stably supported an Ebola viral cDNA of 20 kb (Neumann et al., 2000) and is therefore suitable for the insertion of large DNA fragments. The generation of pTM-PolI-WSN-All (FIG. 3A; about 22.5 kb in length), which contains eight individual RNA polymerase I transcription units, did not present major obstacles; however, growth of E. coli JM109 bacteria at room temperature was required to prevent recombination of this plasmid.

Figure 3:
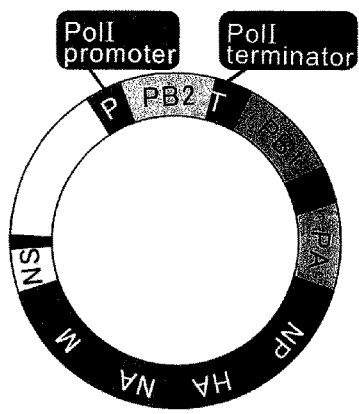
FIG. 3. Schematic diagrams of plasmids possessing multiple influenza viral genes. A) pTM-PolI-WSN-All for the transcription of all eight influenza viral RNAs from one template. Transcription units comprising the human RNA polymerase I promoter (blue, Pol I promoter), a cDNA encoding an influenza viral segment in negative-sense orientation (shown in different colors), and the mouse RNA polymerase I terminator (black, Pol I terminator) were combined on one plasmid by using unique recognition sites for restriction endonucleases. B) pTM-PolI-WSN-PB2-PB1-PA-NP-M-NS and pTM-PolI-WSN-HA-NA for the transcription of six and two influenza viral RNAs from one plasmid. These plasmids and the terminology were generated as outlined for pTM-PolI-WSN-All. C. pC-PolII-WSN-PB2-PB1-PA for the transcription of PB2, PB1, and PA mRNAs from one plasmid. Transcription units comprising an RNA polymerase II promoter (dark blue, Pol II promoter), i.e., the chicken β-actin promoter, the coding region for the respective viral protein (shown in different colors), and a polyadenylation sequence (gold, PolyA) were combined on one plasmid by using unique recognition sites for restriction endonucleases.
Figure 3:
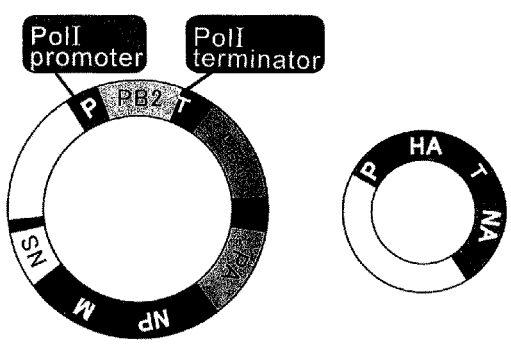
Figure 3:
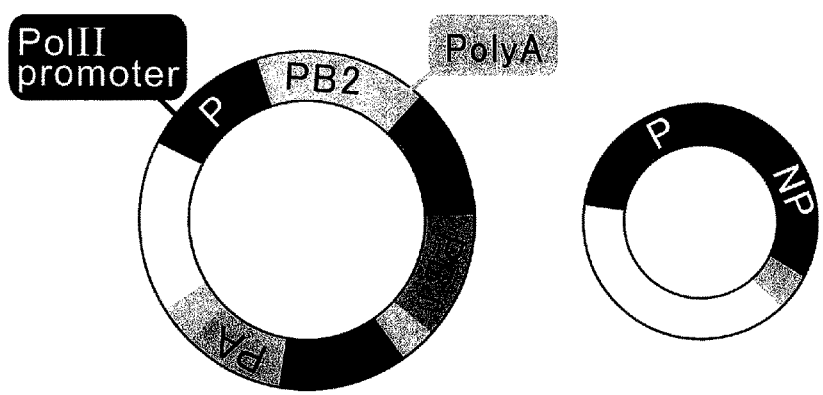

For the annual generation of influenza virus vaccines, only two viral RNA segments, i.e., those encoding the hemagglutinin (HA) and neuraminidase (NA) surface glycoproteins, need to be replaced. For this reason, a plasmid was generated in which the transcription units for the HA and NA segments were combined (pTM-PolI-WSN-HA-NA) (FIG. 3B), while a second plasmid combined the transcription units encoding the internal proteins (pTM-PolI-WSN-PB2-PB1-PA-NP-M-NS) (FIG. 3B). Both of these plasmids were stable during amplification in E. coli JM109 bacteria at 37° C.

To further reduce the number of plasmids required for virus generations, the three RNA polymerase II transcription units for the WSN PB2, PB1, and PA proteins were combined on one vector backbone, using the same strategy that allowed the joining of the RNA polymerase I transcription units for vRNA synthesis. The resulting plasmid was stable in E. coli JM109 bacteria at 37° C.; it was designated pC-PolII-WSN-PB2-PB1-PA (FIG. 3C). Of note, a plasmid combining the RNA polymerase II transcription unit for the polymerase proteins and NP was unable to be recovered.

Virus Generation in 293T Cells from Plasmids Containing Multiple Transcription Cassettes.

To test the functionality of plasmids containing multiple transcription cassettes, 293T cells were transfected with pTM-PolI-WSN-All (for the transcription of all eight vRNAs) (Table 1, columns 2 and 3), or pTM-PolI-WSN-HA-NA and pTM-PolI-WSN-PB2-PB1-PA-NP-M-NS (for the transcription of two and six vRNAs) (Table 1, columns 7 and 8). Cells were cotransfected with 4 plasmids for the expression of NP and the polymerase subunits from separate plasmids (Table 1, columns 2 and 7), or with 2 plasmids that express NP, or PB2, PB1, and PA, respectively (Table 1, columns 3 and 8). Viruses were successfully generated from these plasmids, demonstrating that RNA polymerase I or RNA polymerase II transcription units can be combined, thus reducing the number of plasmids required for the artificial generation of influenza virus. At forty-eight hours post-transfection, the efficiency of virus generation ranged from $2 \times 10^7$ to $2.7 \times 10^8$ $TCID_{50}/ml$ (Table 1, columns 2, 3, 7, 8: mean=$1.1 \times 10^8$ $TCID_{50}/ml$). These efficiencies were slightly higher (p=0.17) than those obtained for control experiments in which cells were transfected with 8 separate plasmids for the transcription of the influenza vRNAs, and four or two plasmids for the synthesis of NP and the three polymerase subunits (Table 1, columns 9 and 10, yielding $6.3 \times 10^6$ to $1.3 \times 10^8$ $TCID_{50}/ml$; mean=$5.5 \times 10^7$ $TCID_{50}/ml$).

A number of control experiments were also carried out including mock-transfections (Table 1, column 14), cells transfected with protein expression plasmids only (Table 1, columns 11 and 12), with 8 plasmids for vRNA synthesis only (Table 1, column 13), or with plasmids for the synthesis of two or six vRNAs, respectively (Table 1, column 4 or 5, respectively). None of these controls yielded viruses. However, appreciable virus titers were consistently detected in cells transfected with pTM-PolI-WSN-All (Table 1, column 1), or with a combination of pTM-PolI-WSN-HA-NA and pTM-PolI-PB2-PB1-PA-NP-M-NS (Table 1, column 6). These plasmids were designed for the transcription of negative-sense viral RNAs, and synthesis of NP and the three polymerase proteins was not expected. Thus, virus generation with these plasmids alone was not expected either (for possible explanations, see below).

TABLE 1

Efficiency of virus generation in 293T cells.

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| vRNA synthesis | | | | | | | | | | | | | | |
| '8 Unit' Plasmid | + | + | + | | | | | | | | | | | |
| '6 Unit' Plasmid | | | | + | | + | + | + | | | | | | |
| '2 Unit' Plasmid | | | | | + | + | + | + | | | | | | |
| 8 × 1 Unit Plasmid | | | | | | | | | + | + | | | + | |
| Protein synthesis | | | | | | | | | | | | | | |
| pCAWS-PB2 | | + | | | | | + | | + | | + | | | |
| pCAWS-PB1 | | + | | | | | + | | + | | + | | | |
| pCAWS-PA | | + | | | | | + | | + | | + | | | |
| pCAWS-NP | | + | | + | | | + | + | + | + | + | + | | |
| pC-PolII-WSN-PB2-PB1-PA | | | + | | | | | + | | + | | + | | |
| Total number of plasmids | 1 | 5 | 3 | 1 | 1 | 2 | 6 | 4 | 12 | 10 | 4 | 2 | 8 | 0 |
| Exp. 1. TCID$_{50}$/ml (48 h p.t.) | $3.2 \times 10^6$ | $2 \times 10^7$ | $4.6 \times 10^7$ | 0 | 0 | $3.7 \times 10^4$ | $5.6 \times 10^7$ | $6.3 \times 10^7$ | $6.3 \times 10^6$ | $6.3 \times 10^6$ | 0 | 0 | 0 | 0 |
| Exp. 2. TCID$_{50}$/ml (48 h p.t.) | $3.7 \times 10^7$ | $2.1 \times 10^8$ | $1.5 \times 10^8$ | 0 | 0 | $1.6 \times 10^5$ | $6.3 \times 10^7$ | $6.3 \times 10^7$ | $6.3 \times 10^7$ | $6.3 \times 10^7$ | 0 | 0 | 0 | 0 |
| Exp. 3. TCID$_{50}$/ml (48 h p.t.) | $6.3 \times 10^4$ | $2.7 \times 10^8$ | $3.2 \times 10^7$ | 0 | 0 | $3.2 \times 10^5$ | $1.6 \times 10^8$ | $1.3 \times 10^8$ | $6.3 \times 10^7$ | $1.3 \times 10^8$ | 0 | 0 | 0 | 0 |

293T cells were transfected with the indicated plasmids. Forty-eight hours later, virus titers in the supernatant were determined by plaque assays in MDCK cells. Shown are the results of three independent experiments. '8 Unit' Plasmid: pTM-PolI-WSN-All; '6 Unit' plasmid: pTM-PolI-WSN-PB2-PB1-PA-NP-M-NS; '2 Unit' plasmid: pTM-PolI-WSN- HA-NA; 8 × 1 Unit Plasmid: Combination of pPolI-WSN-PB2, -PB1, -PA, -HA, -NP, -NA, -M, -NS; p.t.: post-transfection.

Virus Generation in Vero Cells from Plasmids Containing Multiple Transcription Cassettes.

Next, the efficiency of virus generation was tested in Vero cells, which are difficult to transfect to high efficiencies. At 48 hours post-transfection, virus generation from 12 plasmids was negligible in two experiments and low in one experiment (Table 2, column 9), while at 72 hours post-transfection, virus was detected in all three experiments. The use of only one or two plasmids for the synthesis of viral RNAs increased the efficiency of virus generation at 72 hours post-transfection, especially in combination with pC-PolII-WSN-PB2-PB1-PA, yielding up to $2.5 \times 10^6$ TCID$_{50}$/ml (Table 2, column 9 vs. 3: p=0.0017; column 9 vs. 8: p=0.0063). Consistently, expression of the three polymerase proteins from plasmid pC-PolII-WSN-PB2-PB1-PA resulted in more efficient virus generation as compared to providing these proteins from separate plasmids (Table 2, compare columns 2 and 3 (p=0.0054), columns 7 and 8 (p=0.028), and columns 9 and 10 (p=0.2)). Virus was detected from plasmid pTM-PolI-WSN-All only (Table 2, column 1), or from plasmids pTM-PolI-WSN-PB2-PB1-PA-NP-M-NS and pTM-PolI-WSN-HA-NA (Table 2, column 6); however, virus generation was not observed consistently and the resulting virus titers were low. This was likely due to the lower transfection efficiency of the Vero cells. Taken together, these results show that plasmids containing multiple RNA polymerase I or II transcription units can be highly efficient at generating virus in Vero cells.

TABLE 2

Efficiency of virus generation in Vero cells.

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| vRNA synthesis | | | | | | | | | | | | | | |
| '8 Unit' Plasmid | + | + | + | | | | | | | | | | | |
| '6 Unit' Plasmid | | | | + | | + | + | + | | | | | | |
| '2 Unit' Plasmid | | | | | + | + | + | + | | | | | | |
| 8 × 1 Unit Plasmid | | | | | | | | | + | + | | | + | |
| Protein synthesis | | | | | | | | | | | | | | |
| pCAWS-PB2 | | + | | | | | + | | + | | + | | | |
| pCAWS-PB1 | | + | | | | | + | | + | | + | | | |
| pCAWS-PA | | + | | | | | + | | + | | + | | | |
| pCAWS-NP | | + | | + | | | + | + | + | + | + | + | | |
| pC-PolII-WSN-PB2-PB1-PA | | | + | | | | | + | | + | | + | | |
| Total number of plasmids | 1 | 5 | 3 | 1 | 1 | 2 | 6 | 4 | 12 | 10 | 4 | 2 | 8 | 0 |
| Exp. 1. TCID$_{50}$/ml (48 h p.t.) | <50 | $1.7 \times 10^4$ | $3.7 \times 10^4$ | 0 | 0 | 0 | <10 | $3.2 \times 10^4$ | <10 | <50 | 0 | 0 | 0 | 0 |
| Exp. 2. TCID$_{50}$/ml (48 h p.t.). | 0 | <50 | $3.7 \times 10^4$ | 0 | 0 | 0 | $6.2 \times 10^2$ | $4.4 \times 10^4$ | <10 | $1.5 \times 10^3$ | 0 | 0 | 0 | 0 |
| Exp. 3. TCID$_{50}$/ml (48 h p.t.). | 0 | $3 \times 10^2$ | $5.1 \times 10^4$ | 0 | 0 | 0 | $1.6 \times 10^2$ | $2 \times 10^4$ | $2 \times 10^3$ | $2.5 \times 10^3$ | 0 | 0 | 0 | 0 |
| Exp. 1. TCID$_{50}$/ml (72 h p.t.) | $3.2 \times 10^4$ | $6.3 \times 10^5$ | $2.5 \times 10^6$ | 0 | 0 | 0 | $5.3 \times 10^3$ | $3.9 \times 10^5$ | $2.5 \times 10^3$ | $6.3 \times 10^4$ | 0 | 0 | 0 | 0 |

TABLE 2-continued

Efficiency of virus generation in Vero cells.

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Exp. 2. TCID$_{50}$/ml (72 h p.t.) | <10 | $3.1 \times 10^3$ | $1.6 \times 10^6$ | 0 | 0 | 0 | $7.6 \times 10^4$ | $6.3 \times 10^5$ | $6.3 \times 10^3$ | $2.1 \times 10^5$ | 0 | 0 | 0 | 0 |
| Exp. 3. TCID$_{50}$/ml (72 h p.t.) | 50 | $3.2 \times 10^4$ | $2 \times 10^6$ | 0 | 0 | 50 | $2 \times 10^4$ | $5.1 \times 10^5$ | $1.6 \times 10^5$ | $2.5 \times 10^5$ | 0 | 0 | 0 | 0 |

Vero cells were transfected with the indicated plasmids. At 48 h or 72 h post-transfection, virus titers in the supernatant were determined by plaque assays in MDCK cells. Shown are the results of three independent experiments. '8 Unit' Plasmid: pTM-PolI-WSN-All; '6 Unit' plasmid: pTM-PolI-WSN-PB2-PB1-PA-NP-M-NS; '2 Unit' plasmid: pTM-PolI-WSN-HA-NA; 8 × 1 Unit Plasmid: Combination of pPolI-WSN-PB2, -PB1, -PA, -HA, -NP, -NA, -M, -NS; p.t.: post-transfection.

Discussion

The generation of vaccine viruses can now be achieved by reverse genetics. In fact, this is the only efficient approach for the production of vaccine strains to highly-pathogenic avian influenza viruses. These viruses are lethal to humans and embryonated eggs (Shortridge et al., 1998); therefore, attenuation, for example, by altering their HA cleavage site sequence (Horimoto et al., 1994; Subbarao et al., 2003), is critical to ensure growth to high titers in embryonated eggs while protecting vaccine production staff against exposure to aerosolized virus. For human use, the production of vaccine strains will require cell lines that are certified for lack of tumorgenicity and adventitious infectious agents. One such cell line is a Vero cell line, which is currently used for the production of rabies and polio vaccines (Montagnon et al., 1999). Using a '12 plasmid' approach, Fodor et al. (1999) reported the generation of 10-20 plaque forming units from $10^7$ Vero cells on day 4 post-transfection. Wood and Robertson (2004) generated an H5N1 reference vaccine strain in Vero cells by reverse genetics but did not report the rescue efficiency, while A/PR/8/34 (H1N1) or A/PR/8/34-based viruses were generated in Vero cells with an efficiency of <$10^3$ pfu/ml (Ozaki et al., 2004). By combining RNA polymerase I and/or II transcription units and thus achieving virus rescue from fewer plasmids, we were able to produce about $10^5$-$10^6$ TCID$_{50}$/ml from $5 \times 10^5$ Vero cells on day 3 post-transfection. Thereby, more efficient virus generation was achieved in Vero cells with these systems as compared with the '12 plasmid' approach (Table 2, compare column 3 or 8 with column 9). This robust and highly efficient reverse genetics system could, therefore, be an asset for the rapid preparation of vaccine strains in pandemic situations.

Influenza virus generation relies on the expression of the polymerase and NP proteins. The combination of the polymerase subunits on one plasmid enhanced the efficiency of virus generation. This finding may be explained by the reduction in the number of plasmids used for virus rescue, or the combination of the three transcription units may more closely reflect the equimolar ratios of polymerase subunits found in infected cells.

The combination of identical promoter and terminator units on one plasmid is thought to cause recombination. However, herein it was demonstrated that eight RNA polymerase I, or three RNA polymerase II promoter and terminator sequences can be combined on one vector backbone. Hoffmann et al. (2000) demonstrated that a combination of RNA polymerase I and II promoters allows vRNA and mRNA synthesis from one template. One could therefore design a plasmid that contains four RNA polymerase I/II transcription units for the synthesis of PB2, PB1, PA, and NP vRNAs and mRNAs, and four RNA polymerase I transcription units for the synthesis of NA, HA, M, and NS vRNAs. Such a construct should allow for the efficient generation of influenza virus from one plasmid. Moreover, the success described herein in combining transcription units on one plasmid may provide the incentive for others to apply this strategy to other reverse genetics systems that rely on the cotransfection of cells with several plasmids, or to design vectors for the simultaneous expression of several proteins from one plasmid.

Surprisingly, virus generation was observed from a single plasmid, pTM-PolI-WSN-All. The expression of influenza viral proteins from this plasmid suggests protein synthesis from a (cryptic) RNA polymerase II promoter present in the vector, or in the RNA polymerase I promoter or terminator region. To determine if the RNA polymerase I promoter sequence harbors a promoter in the opposite direction that could potentially drive protein expression from the upstream transcription cassette, we cloned an inverted RNA polymerase I promoter in front of a reporter gene; however, appreciable levels of reporter gene expression was not detected from this plasmid (data not shown). The generation of influenza virus relies on the expression of four different proteins (PB2, PB1, PA, and NP) and would therefore require several read-through events. Alternatively, protein expression may have resulted from another mechanism, such as internal initiation of translation. A modified pTM1 (Moss et al., 1990) vector was used that contains the fl single-strand DNA origin of replication, the ampicillin resistance gene, a multiple cloning site, and the T7 RNA polymerase transcriptional terminator. The strong T7 RNA polymerase promoter and parts of the EMCV untranslated region and thymidine kinase sequences that are present in the original pTM1 cloning vector had been eliminated from this modified version. Protein synthesis of the polymerase and NP proteins from this vector was therefore not expected. Nonetheless, the generation of influenza virus from plasmids designed to produce only negative-strand RNAs is intriguing and deserves further study.

In summary, here, an improved system for the generation of influenza viruses is described herein that allows the easy and reproducible production of vaccine viruses in Vero cells. Application of this system may be especially advantageous in situations of outbreaks of highly pathogenic avian influenza viruses.

EXAMPLE 2

To improve recombinant virus production, one approach is to clone cDNAs encoding all eight viral genes into a plasmid. Thus, instead of generating 8 viral RNAs from eight plasmids, the transcription unit for the synthesis of the viral RNAs can be combined on one plasmid; hence, all eight viral RNAs are made from only one plasmid, allowing virus rescue from fewer plasmids. Likewise, the transcription units for the synthesis of viral proteins can be combined on fewer plasmids. If all 8 viral genes are similarly placed in 1 plasmid, the number of plasmids required for synthesis of influenza virus is 5 (1 plasmid for all viral genes and 4 plasmids for genes encoding PB2, PB1, PA, and NP). Alternatively, one can combine PB2, PB1, PA, and NP genes into 1 plasmid, each gene flanked by a RNA polymerase II promoter and a polyadenylation signal. Furthermore, all viral genes and PB2, PB1, PA, and NP can be combined into 1 plasmid. Other combinations can include 1 plasmid with six viral genes each with a Pol I promoter, 1 plasmid with 3 viral genes each with a Pol II promoter, and 1 plasmid with 2 viral genes (HA and NA) each with a Pol I promoter.

Figure 4:
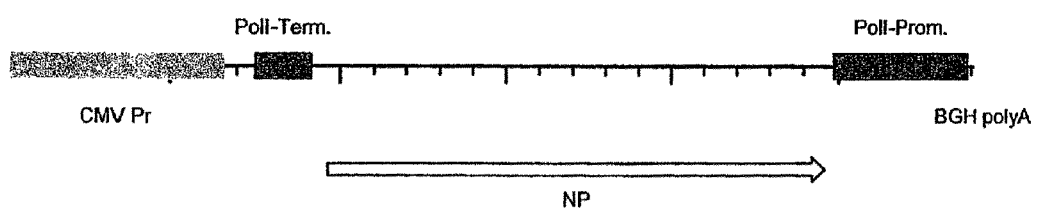
FIG. 4. RNA polymerase I/II transcription unit. The NP gene is flanked by RNA polymerase I terminator (PolI-Term) and RNA polymerase I promoter (PolI-Prom) sequences. This unit is then inserted between an RNA polymerase II promoter, such as the CMV promoter (CMV Pr), and a polyadenylation signal, such as the bovine growth hormone polyadenylation signal (BGH polyA).
Figure 5:
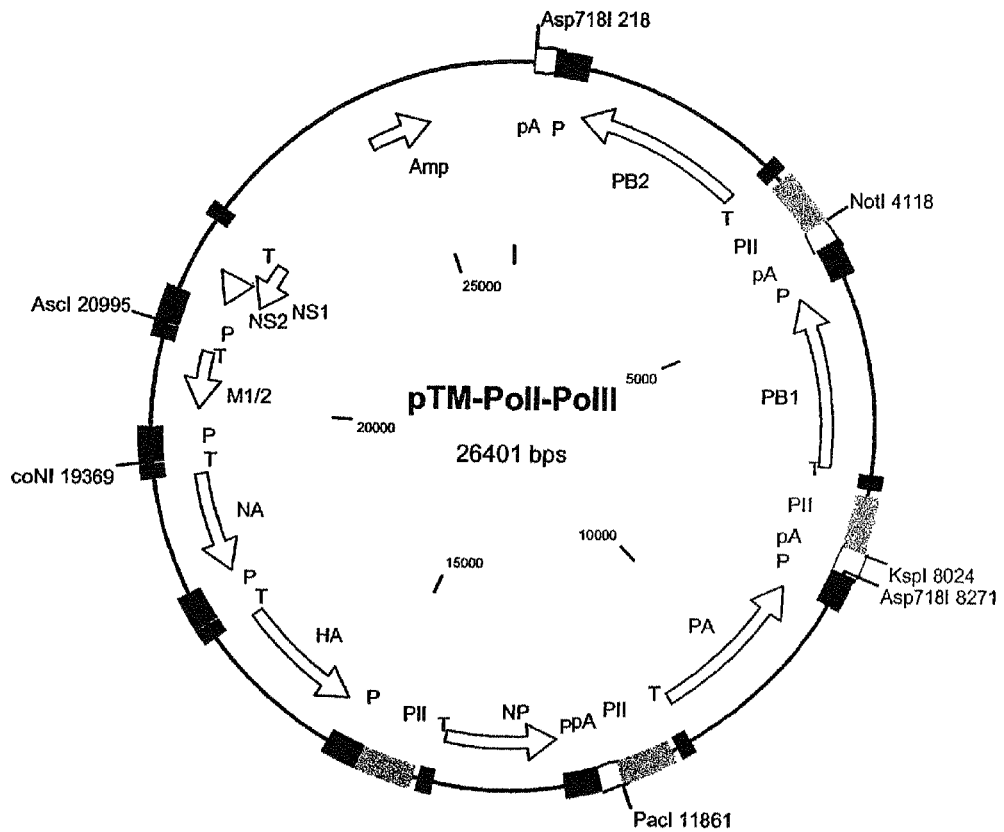
FIG. 5. Plasmid containing four RNA polymerase I/II transcription units for the synthesis of PB2, PB1, PA, and NP vRNAs and mRNAs, and four RNA polymerase I transcription units for the synthesis of HA, NA, M, and NS vRNAs. PII:RNA polymerase II promoter (shaded box), pA:polyadenylation signal (open box); P:RNA polymerase I promoter (large black box), T:RNA polymerase I terminator (small black box).

A viral gene is flanked by RNA polymerase I promoter and terminator sequences to form a transcription unit (or cassette), and in some embodiments, that transcription cassette is then flanked by a RNA polymerase II promoter and termination signal (polyadenylation signal) (FIG. 4). This approach yields both genomic negative strand RNA synthesized by RNA polymerase I and mRNA synthesized by RNA polymerase II from the same gene.

Thus, the present invention reduces the number of plasmids for transfection from 12 to 5 or fewer, e.g., 4, 3, 2 or 1, increases the rescue efficiency of virus from cell lines allowing generation of severely attenuated virus, allows use of cell lines with low transfection efficiency (e.g., Vero cells), allows consistent generation of influenza virus for vaccine production, and/or reduces FDA regulatory issues regarding plasmid history, purity, and toxicity.

REFERENCES

Albo et al., *J. Virol.*, 70:9013 (1996).
Avery's Drug Treatment: Principles and Practice of Clinical Pharmacology and Therapeutics, 3rd edition, ADIS Press, Ltd., Williams and Wilkins, Baltimore, Md. (1987).
Aymard-Henry et al., *Virology: A Practical Approach*, Oxford IRL Press, Oxford, 119-150 (1985).
Bachmeyer, *Intervirology*, 5:260 (1975).
Berkow et al., eds., *The Merck Manual*, 16th edition, Merck & Co., Rahway, N.J. (1992).
Brands et al., *Dev. Biol. Stand.*, 98:93 (1999).
Bridgen et al., *Proc. Natl. Acad. Sci. U.S.A*, 93:15400 (1996).
Bruhl et al., *Vaccine*, 19:1149 (2000).
Claas et al., *Lancet*, 351:472 (1998).
Dunn et al., *Virology*, 211:133 (1995).
Edwards, *J. Infect. Dis.*, 169: 68 (1994).
Elliott, *Mol. Med.*, 3:572 (1997).
Enami et al., *Proc. Natl. Acad. Sci. U.S.A.*, 87:3802 (1990).
Fodor et al., *J. Virol.*, 73:9679 (1999).
Fouchier et al., *Proc. Natl. Acad. Sci. USA*, 101:1356 (2004).
Gerdil, *Vaccine*, 21:1776 (2003).
Grand and Skehel, *Nature, New Biology*, 238:145 (1972).
Hagen et al., *J. Virol.*, 68:1509 (1994).
Halperin et al., *Vaccine*, 20:1240 (2002).
Hoffman et al., *Proc. Natl. Acad. Sci. USA*, 97:6108 (2000).
Hoffman et al., *Proc. Natl. Acad. Sci. USA*, 99:11411 (2002).
Honda et al., *J. Biochem.* (Tokyo), 104:1021 (1988).
Horimoto et al., *J. Virol.*, 68:3120 (1994).
Kilbourne, *Bull. M2 World Health Org.*, 41: 653 (1969).
Kistner et al., *Dev. Biol. Stand.*, 98:101 (1999).
Kistner et al., *Vaccine*, 16:960 (1998).
Kistner et al., *Wein. Klin. Wochenschr.*, 111:207 (1999).
Koopmans et al., *Lancet*, 363:587 (2004).
Laver & Webster, *Virology*, 69:511 (1976).
Lawson et al., *Proc. Natl. Acad. Sci. U.S.A.*, 92:4477 (1995).
Leahy et al., *J. Virol.*, 71:8347 (1997).
Leahy et al., *J. Virol.*, 71:8352 (1997).
Leahy et al., *J. Virol.*, 72:2305 (1998).
Mizrahi, (ed.), *Viral Vaccines*, Wiley-Liss, New York, 39-67 (1990).
Montagnon et al., *Dev. Biol. Stand.*, 98:137 (1999).
Moss et al., *Nature*, 348:91 (1990).
Murphy, *Infect. Dis. Clin. Pract.*, 2: 174 (1993).
Muster et al., *Proc. Natl. Acad. Sci. USA*, 88: 5177 (1991).
Neumann et al., *Adv. Virus Res.*, 53:265 (1999).
Neumann et al., *J. Gen. Virol.*, 83:2635 (2002).
Neumann et al., *J. Virol.*, 76:406 (2002).
Neumann et al., *Proc. Natl. Acad. Sci. USA*, 96:9345 (1999).
Nicolson et al., *Vaccine*, 23:2943 (2005).
Ogra et al., *J. Infect. Dis.*, 134: 499 (1977).
Osol (ed.), *Remington's Pharmaceutical Sciences*, Mack Publishing Co., Easton, Pa. 1324-1341 (1980).
Ozaki et al., *J. Virol.*, 78:1851 (2004).
Palache et al., *Dev. Biol. Stand.*, 98:115 (1999).
Peiris et al., *Lancet*, 363:617 (2004).
Potter in *Textbook of Influenza*, eds. Nicholson, K. G., Webster, R. G. & Hey, A. J.; Malden: Blackwell Scientific Publication, pp. 3-18 (1998).
Robertson et al., *Biologicals*, 20:213 (1992).
Robertson et al., *Giornale di Igiene e Medicina Preventiva*, 29:4 (1988).
Schnell et al., *EMBO J.*, 13:4195 (1994).
Shortridge et al., *Virology*, 252:331 (1998).
Subbarao et al., *J. Virol.*, 67:7223 (1993).
Subbarao et al., *Science*, 279:393 (1998).
Subbarao et al., *Virology*, 305:192 (2003).
Sugawara et al., *Biologicals*, 30:303 (2002).
Thompson et al., *Jama*, 289:179 (2003).
Weber et al., *Arch. Virol.*, 142:1029 (1997).
Weber et al., *J. Virol.*, 70:8361 (1996).
Weber et al., *Arch. Virol.*, 142:1029 (1997).
World Health Organization TSR No. 673 (1982).
WHO, Cumulative Number of Confirmed Human Cases of Avian Influenza A (H5N1) since 28 Jan. 2004.
Wood & Robertson, *Nat. Rev. Microbiol.*, 2:842 (2004).
Yasuda et al., *J. Virol.*, 68:8141 (1994).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A set of three plasmids for influenza virus production together having eight transcription cassettes for influenza virus vRNA production and four transcription cassettes for influenza virus mRNA production, wherein the transcription cassettes for vRNA production include a transcription cassette comprising a PolI promoter operably linked to an influenza virus PA cDNA linked to a PolI transcription termination sequence, a transcription cassette comprising a PolI promoter operably linked to an influenza virus PB1 cDNA linked to a PolI transcription termination sequence, a transcription cassette comprising a PolI promoter operably linked to an influenza virus PB2 cDNA linked to a PolI transcription termination sequence, a transcription cassette comprising a PolI promoter operably linked to an influenza virus HA cDNA linked to a PolI transcription termination sequence, a transcription cassette comprising a PolI promoter operably linked to an influenza virus NP cDNA linked to a PolI transcription termination sequence, a transcription cassette comprising a PolI promoter operably linked to an influenza virus NA cDNA linked to a PolI transcription termination sequence, a transcription cassette comprising a PolI promoter operably linked to an influenza virus M cDNA linked to a PolI transcription termination sequence, and a transcription cassette comprising a PolI promoter operably linked to an influenza virus NS cDNA linked to a PolI transcription termination sequence; wherein the transcription cassettes for mRNA production include a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and a transcription cassette comprising a PolII promoter operably linked to a DNA coding region for influenza virus NP linked to a PolII transcription termination sequence, and wherein transfection of a cell with the three plasmids yields titers of at least $1 \times 10^2$ TCID$_{50}$/mL.

2. The set of claim 1, wherein one plasmid has eight transcription cassettes for vRNA production.

3. The set of claim 2, wherein one plasmid has one transcription cassette for mRNA production and another plasmid has three transcription cassettes for mRNA production.

4. The set of claim 1, wherein one plasmid has six transcription cassettes for vRNA production and another plasmid has two transcription cassettes for vRNA production.

5. The set of claim 4, wherein one plasmid has four transcription cassettes for mRNA production.

6. The set of claim 1, wherein the HA is a type A HA.

7. The set of claim 1, wherein the HA is a type B HA.

8. A method to prepare influenza virus, comprising: contacting a cell with the set of plasmids of claim 1, or in an amount effective to yield infectious influenza virus.

9. A composition comprising the set of plasmids of claim 1.

10. The set of claim 5, wherein the two transcription cassettes for vRNA production are for HA and NA.

* * * * *

UNITED STATES PATENT AND TRADEMARK OFFICE
CERTIFICATE OF CORRECTION

PATENT NO. : 8,877,209 B2  Page 1 of 1
APPLICATION NO. : 13/113244
DATED : November 4, 2014
INVENTOR(S) : Yoshihiro Kawaoka et al.

It is certified that error appears in the above-identified patent and that said Letters Patent is hereby corrected as shown below:

In the Specification

Column 1, Lines 15-19:
Delete the phrase:
"This invention was made with a grant from the Government of the United States of America (grant AI047446 from the National Institute of Allergy and Infectious Diseases Public Health Service). The Government may have certain rights in the invention."

And replace with:
--This invention was made with government support under AI047446 awarded by the National Institutes of Health. The government has certain rights in the invention.--.

Signed and Sealed this
First Day of December, 2020

Andrei Iancu
*Director of the United States Patent and Trademark Office*

SEQUENCE LISTING

<160> NUMBER OF SEQ ID NOS: 12

<210> SEQ ID NO 1
<211> LENGTH: 33
<212> TYPE: DNA
<213> ORGANISM: Artificial Sequence
<220> FEATURE:

```
<223> OTHER INFORMATION: A synthetic oligonucleotide

<400> SEQUENCE: 1
gggttattgg agacggtacc gtctcctccc ccc                                    33

<210> SEQ ID NO 2
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 2 gggggggagga gacggtaccg tctccaataa ccc                                   33

<210> SEQ ID NO 3
<211> LENGTH: 18
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 7
<223> OTHER INFORMATION: n = A,T,C or G

<400> SEQUENCE: 3
cgtctcntat tagtagaa                                                     18

<210> SEQ ID NO 4
<211> LENGTH: 18
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 12
<223> OTHER INFORMATION: n = A,T,C or G

<400> SEQUENCE: 4
ttctactaat angagacg                                                     18

<210> SEQ ID NO 5
<211> LENGTH: 17
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 11
<223> OTHER INFORMATION: n = A,T,C or G

<400> SEQUENCE: 5
ttttgctccc ngagacg                                                      17

<210> SEQ ID NO 6
<211> LENGTH: 17
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 7
<223> OTHER INFORMATION: n = A,T,C or G

<400> SEQUENCE: 6
```

-continued

```
cgtctcnggg agcaaaa                                                    17

<210> SEQ ID NO 7
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 7
tattagtaga a                                                          11

<210> SEQ ID NO 8
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 8
gggagcaaaa                                                            10

<210> SEQ ID NO 9
<211> LENGTH: 13
<212> TYPE: DNA
<213> ORGANISM: Artificial Sequence
<220> FEATURE:
<223> OTHER INFORMATION: A synthetic oligonucleotide

<400> SEQUENCE: 9
ttttgctccc ccc                                                        13

<210> SEQ ID NO 10
<211> LENGTH: 13
<212> TYPE: DNA
<213> ORGANISM: Artificial Sequence
<220> FEATURE:
<223> OTHER INFORMATION: A synthetic oligonucleotide

<400> SEQUENCE: 10
ggggggagca aaa                                                        13

<210> SEQ ID NO 11
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 11
gggttattag tagaa                                                      15

<210> SEQ ID NO 12
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 12
ttctactaat aaccc                                                      15
```